United States Patent [19]

Nelson

[11] Patent Number: 5,256,790
[45] Date of Patent: Oct. 26, 1993

[54] 27-HYDROXYRAPAMYCIN AND DERIVATIVES THEREOF

[75] Inventor: Frances C. Nelson, Yardley, Pa.

[73] Assignee: American Home Products Corporation, New York, N.Y.

[21] Appl. No.: 9,605

[22] Filed: Jan. 27, 1993

Related U.S. Application Data

[63] Continuation-in-part of Ser. No. 930,124, Aug. 13, 1992, abandoned.

[51] Int. Cl.$^5$ .................. C07D 498/16; A61K 31/695
[52] U.S. Cl. ...................................... 514/291; 540/456
[58] Field of Search ........................ 540/456; 514/291

[56] References Cited

U.S. PATENT DOCUMENTS

| | | |
|---|---|---|
| 3,929,992 | 12/1975 | Sehgal et al. . |
| 3,993,749 | 11/1976 | Sehgal et al. . |
| 4,316,885 | 2/1982 | Rakhit . |
| 4,401,653 | 8/1983 | Eng . |
| 4,650,803 | 3/1987 | Stella et al. . |
| 4,885,171 | 12/1989 | Sehgal et al. . |
| 5,078,999 | 1/1992 | Warner et al. . |
| 5,080,899 | 1/1992 | Sturm et al. . |
| 5,091,389 | 2/1992 | Ondeyka et al. . |
| 5,100,883 | 3/1992 | Schiehser . |
| 5,100,899 | 3/1992 | Calne . |
| 5,102,876 | 4/1992 | Caufield . |
| 5,118,677 | 6/1992 | Caufield . |
| 5,118,678 | 6/1992 | Kao et al. . |
| 5,130,307 | 7/1992 | Failli et al. . |
| 5,138,051 | 8/1992 | Hughes et al. . |
| 5,147,877 | 11/1992 | Goulet ........................... 540/456 |
| 5,151,413 | 9/1992 | Caufield et al. . |
| 5,169,851 | 12/1992 | Hughes et al. . |
| 5,177,203 | 1/1993 | Failli et al. . |
| 5,194,447 | 3/1993 | Kao . |

FOREIGN PATENT DOCUMENTS

507555A1 7/1992 European Pat. Off. .

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Meiser, B. J., J. Heart Lung Transplant. 11 (pt. 2):197 (1992).
Stepkowski, S. M., Transplantation Proc. 23:507-8 (1991).

Primary Examiner—Marianne M. Cintins
Assistant Examiner—John Peabody
Attorney, Agent, or Firm—Arnold S. Milowsky

[57] ABSTRACT

This invention provides a compound of formula I,

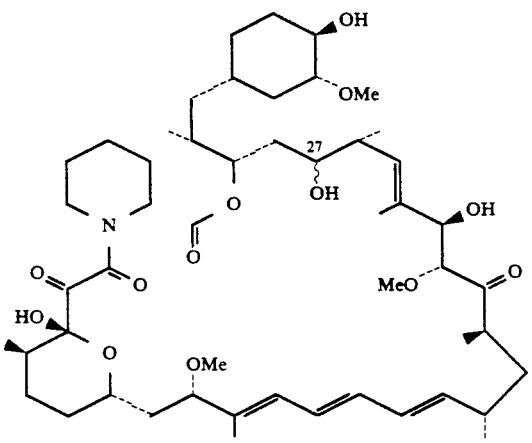

and 27-substituted derivatives thereof which are useful as immunosuppressive, antiinflammatory, antifungal, antitumor, and antiproliferative agents. The compound depicted by formula I is named 27-hydroxyrapamycin, and may also be referred to as 27-deoxo-27-hydroxyrapamycin.

11 Claims, No Drawings

27-HYDROXYRAPAMYCIN AND DERIVATIVES THEREOF

CROSS REFERENCE TO RELATED APPLICATION

This application is a continuation in part of Ser. No. 07/930,124, filed Aug. 13, 1992, now abandoned.

BACKGROUND OF THE INVENTION

This invention relates to a compound of formula I, which is named 27-hydroxyrapamycin, and derivatives thereof and a method for using them for inducing immunosuppression, and in the treatment of transplantation rejection, host vs. graft disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. Under the older numbering convention, 27-hydroxyrapamycin would be named as 24-hydroxyrapamycin.

U.S. Pat. No. 5,102,876 discloses 15-hydroxyrapamycin and 15,27-bis-hydroxyrapamycin, which were prepared by the reduction of rapamycin with diisobutylaluminum hydride, and a method of using them as immunosuppressive, antiinflammatory, and antifungal agents. 27-hydroxyrapamycin cannot be produced via the synthetic methodology disclosed in U.S. Pat. No. 5,102,876.

U.S. Pat. Nos. 5,138,051 and 5,169,851 disclose 33-hydroxyrapamycin which were prepared by the reduction of rapamycin using sodium triacetoxyborohydride, and a method of using them as immunosuppressive, antiinflammatory, and antifungal agents. 27-hydroxyrapamycin cannot be produced via the synthetic methodology disclosed in U.S. Pat. Nos. 5,138,051 and 5,169,851.

DESCRIPTION OF THE INVENTION.

This invention provides a compound of formula I,

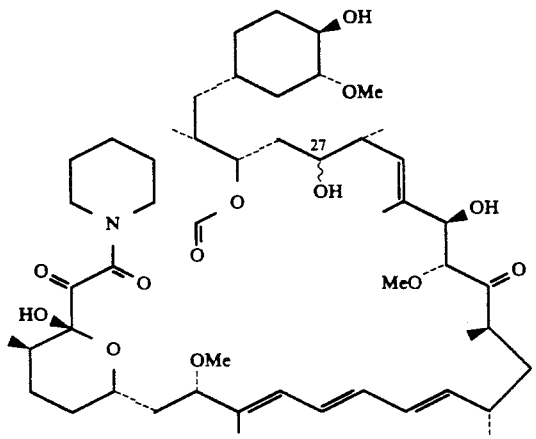

which is useful as an immunosuppressive, antiinflammatory, antifungal, antitumor, and antiproliferative agent. The compound depicted by formula I is named 27-hydroxyrapamycin, and may also be referred to as 27-deoxo-27-hydroxyrapamycin. 27-Hydroxyrapamycin may be administered orally, parenterally, intranasally, intrabronchially, transdermally, or rectally when administered in accordance with this disclosure.

This invention also provides derivatives of 27-hydroxyrapamycin which are useful as immunosuppressive, antiinflammatory, antifungal, antitumor, and antiproliferative agents having the formula II:

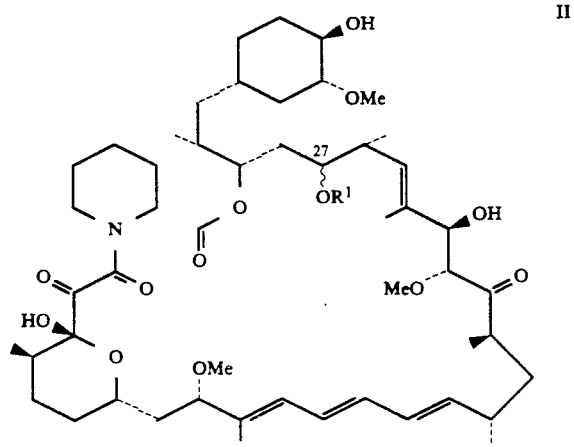

wherein
$R^1$ is

and

R² is alkyl of 1–10 carbon atoms, arylalkyl of 7–10 carbon atoms, or aryl wherein the aryl group may be optionally mono-, di-, or tri- substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO₃H, —PO₃H, and —CO₂H;

or a pharmaceutically acceptable salt thereof;
or having the formula III:

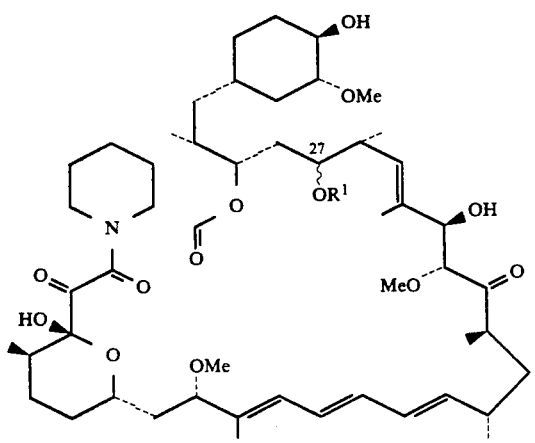

wherein
R¹ is

and
R² is a mono-, di-, poly-, or per-fluorinated alkyl group of 1–10 carbon atoms; or having the formula IV:

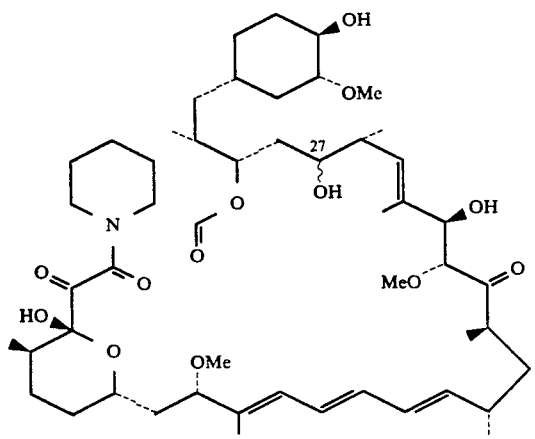

wherein

R¹ is

R² is

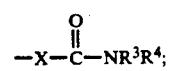

X is —(CH₂)$_m$— or —Ar—;

R³ and R⁴ are each, independently, hydrogen, alkyl of 1–12 carbon atoms, —(CH₂)$_n$—Ar, —(CH₂)$_p$—NR⁵R⁶, or —(CH₂)$_p$—N⁺R⁵R⁶R⁷Y⁻;

R⁵ and R⁶ are each, independently, hydrogen, alkyl of 1–12 carbon atoms, or —(CH₂)$_n$—Ar;

Ar is an optionally mono- or di- substituted group selected from

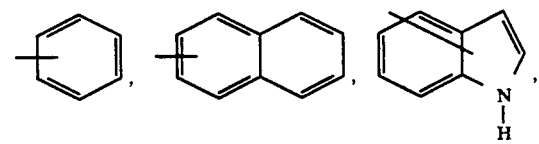

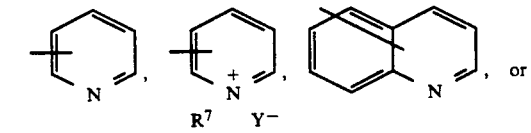

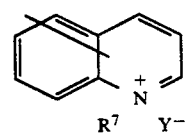

in which the optional substituents are selected from the group consisting of alkyl of 1–6 carbon atoms, arylalkyl of 7–10 carbon atoms, alkoxy of 1–6 carbon atoms, cyano, halo, nitro, carbalkoxy of 2–7 carbon atoms, or perfluoroalkyl of 1–6 carbon atoms;

R⁷ is alkyl of 1–6 carbon atoms;

Y is a halide, sulfate, phosphate, or p-toluenesulfonate anion;

m = 1–6;

n = 1–6;

p = 1–6;

or a pharmaceutically acceptable salt thereof;
or having the formula V:

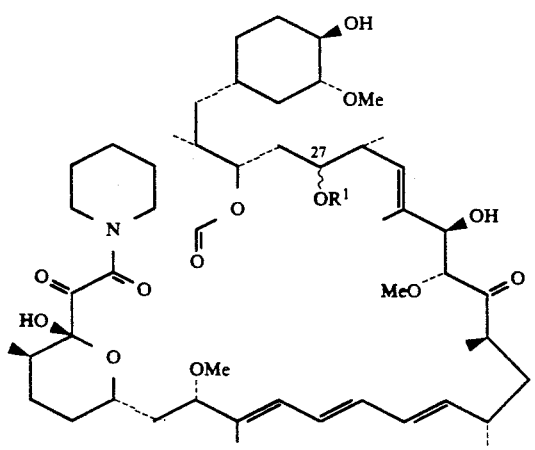 V

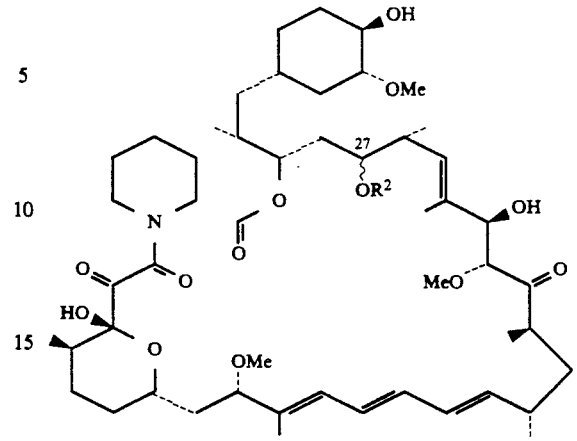 VI wherein
R¹ is

R² is —NH(CR³R⁴)ₙ—X;

R³ and R⁴ are each, independently, hydrogen, alkyl of 1–6 carbon atoms, arylalkyl of 7–10 carbon atoms, cycloalkyl of 3–8 carbon atoms, halogen, or trifluoromethyl;

X is hydrogen, lower alkyl of 1–6 carbon atoms, cycloalkyl of 3–8 carbon atoms, trifluoromethyl, nitro, alkoxy of 1–6 carbon atoms, carboalkoxy of 2–7 carbon atoms, arylalkyl of 7–10 carbon atoms, halo, dialkylamino of 1–6 carbon atoms per alkyl group, thioalkyl of 1–6 carbon atoms, or Y;

Y is a phenyl group which may be optionally mono-, di-, or tri- substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, dialkylamino of 1–6 carbon atoms per alkyl group, or alkylthio of 1–6 carbon atoms, —SO₃H, —PO₃H, and —CO₂H;

n = 0–5;

with the proviso that R¹ and R² are not both hydrogen and when n=0, X is lower alkyl of 1–6 carbon atoms, cycloalkyl of 3–8 carbon atoms, arylalkyl of 7–10 carbon atoms, or Y;

or a pharmaceutically acceptable salt thereof;

or having the formula VI:

wherein
R² is

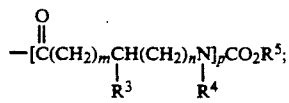

R³ is hydrogen, alkyl of 1–6 carbon atoms, arylalkyl of 7–10 carbon atoms, —(CH₂)_qCO₂R⁶, —(CH₂)ᵣNR⁷CO₂R⁸, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazoylmethyl or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

R⁴ and R⁷ are each, independently, hydrogen, alkyl of 1–6 carbon atoms, or arylalkyl of 7–10 carbon atoms;

R⁵, R⁶, and R⁸ are each, independently, alkyl of 1–6 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

m is 0–4;
n is 0–4;
p is 1–2;
q is 0–4;
r is 0–4;

wherein R³, R⁴, m, and n are independent in each of the

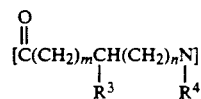

subunits when p=2;

or a pharmaceutically acceptable salt thereof;

or having the formula VII:

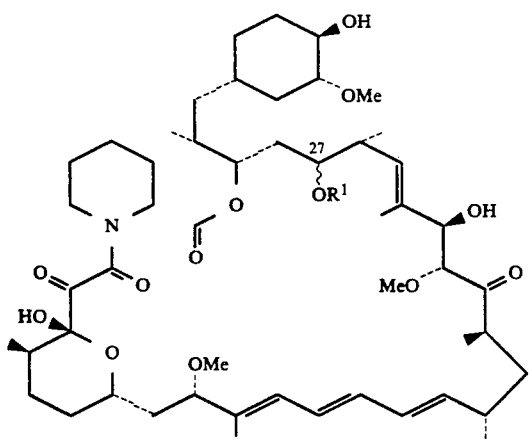

VII

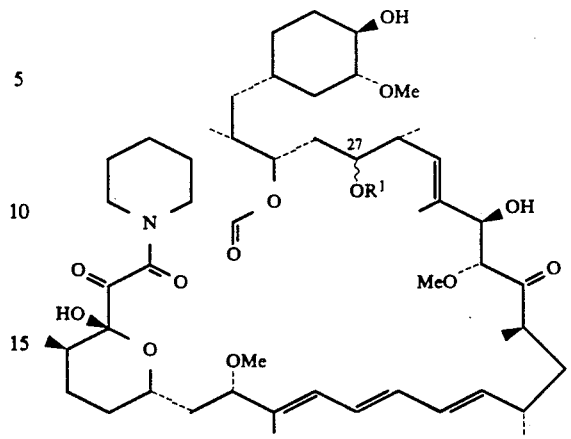

IX wherein
  R¹ is alkyl of 1–6 carbon atoms, arylalkyl of 7–10 carbon atoms, —CH₂YX, —C(CH₃)₂YX, —CH(CH₃)YX, or L;
  Y is O or S;
  X is —CH₃, —(CH₂)ₙCH₃, —CH₂Ar, —(CH₂)₂OCH₃, —CH₂CCl₃, —CH(CH₃)₂, or —CH₂CH₂SiMe₃;
  L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S dioxide; and
  n = 1–5;
or having the formula VIII:

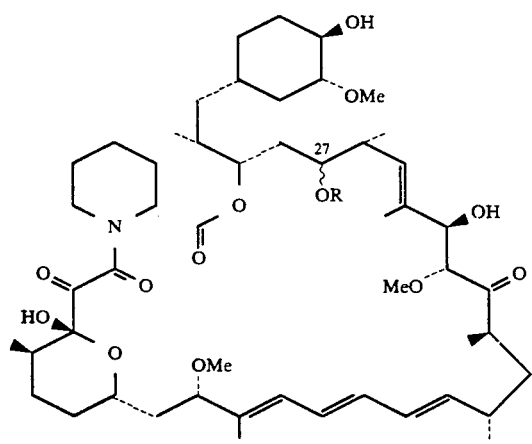

VIII wherein
R is

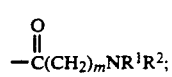

R¹ and R² are each hydrogen or alkyl of 1–3 carbon atoms or R¹ and R² together with the nitrogen to which they are attached form a saturated heterocyclic ring having 4–5 carbon atoms; and
m = 1–3 or a pharmaceutically acceptable salt thereof;
or having the formula IX:

wherein
  R¹ is —CONHSO₂—Ar; and
  Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO₃H, —PO₃H, and —CO₂H;
  or a pharmaceutically acceptable salt thereof when the Ar group contains a basic nitrogen or when the Ar group is substituted by dialklyamino of 1–6 carbon atoms per alkyl group, —SO₃H, —PO₃H, or —CO₂H;
  or a pharmaceutically acceptable salt thereof;
or having formula X:

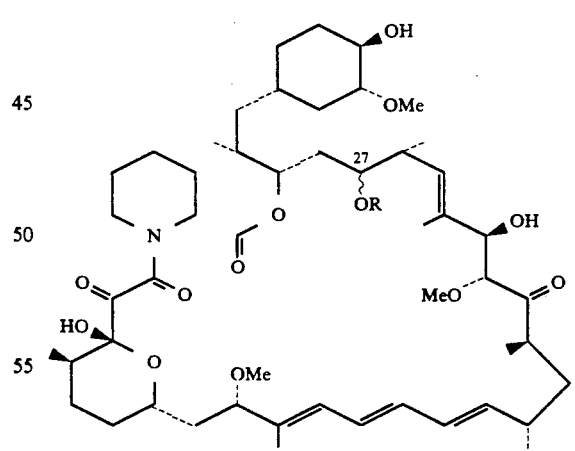

X wherein
  R is —SO₂R¹;
  R¹ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR²; and
  R² is lower alkyl containing 1 to 6 carbon atoms;
  or a pharmaceutically acceptable salt thereof.

Pharmaceutically acceptable salts may be formed from the compounds of formulas II, IV–VI, and VII–X from organic and inorganic acids and inorganic cations. Preferred organic and inorganic acids are those such as acetic, lactic, citric, tartaric, succinic, maleic, malonic, gluconic, hydrochloric, hydrobromic, phosphoric, nitric, sulfuric, methanesulfonic, and the like. Preferred inorganic cations are those such as sodium, potassium, and the like. Based on this disclosure, other pharmaceutically acceptable salts that can be formed will be readily apparent to one skilled in the art.

When any of the compounds of formulas II–X contain an aryl or arylalkyl moiety, it is preferred that the aryl portion is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl group that may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —$SO_3H$, —$PO_3H$, and —$CO_2H$. It is more preferred that the aryl moiety is a phenyl group that is optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —$SO_3H$, —$PO_3H$, and —$CO_2H$.

For the compounds of formula IV, preferred members are those in which X is —$(CH_2)_m$— and $R^3$ and $R^4$ are alkyl of 1–6 carbon atoms; and those in which X is —$(CH_2)_m$—, $R^3$ is hydrogen, and $R^4$ is and Ar is —$(CH_2)_n$—Ar.

For the compounds of formula V, preferred members are those in which n is 0 and X is Y.

For the compounds of formula VI, preferred members are those in which m=0, n=0, and p=1; m=0, n=0, and p=2; n=0, and $R^3$ is —$(CH_2)_q CO_2 R^6$; m=0, n=0, and $R^3$ is —$(CH_2)_r NR^7 CO_2 R^8$; and m=0, n=0, and $R^3$ is hydrogen.

For the compounds of formula VII, preferred members include those in which Y is O and those in which $R^1$ is alkyl of 1–6 carbon atoms.

The compounds of formulas II–X may be administered orally, parenterally, intranasally, intrabronchially, transdermally, or rectally when administered in accordance with this disclosure.

This invention also provides pharmaceutical compositions comprising an effective amount of 27-hydroxyrapamycin or any of the compounds of formulas II–X, and a pharmaceutical carrier.

It is contemplated that when the compounds of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, rapamycin, cyclosporin A, FK-506, OKT-3, and ATG. By combining 27-hydroxyrapamycin or a derivative thereof with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The preparation of 27-hydroxyrapamycin can be accomplished by the sequence of reactions shown below, beginning with rapamycin.

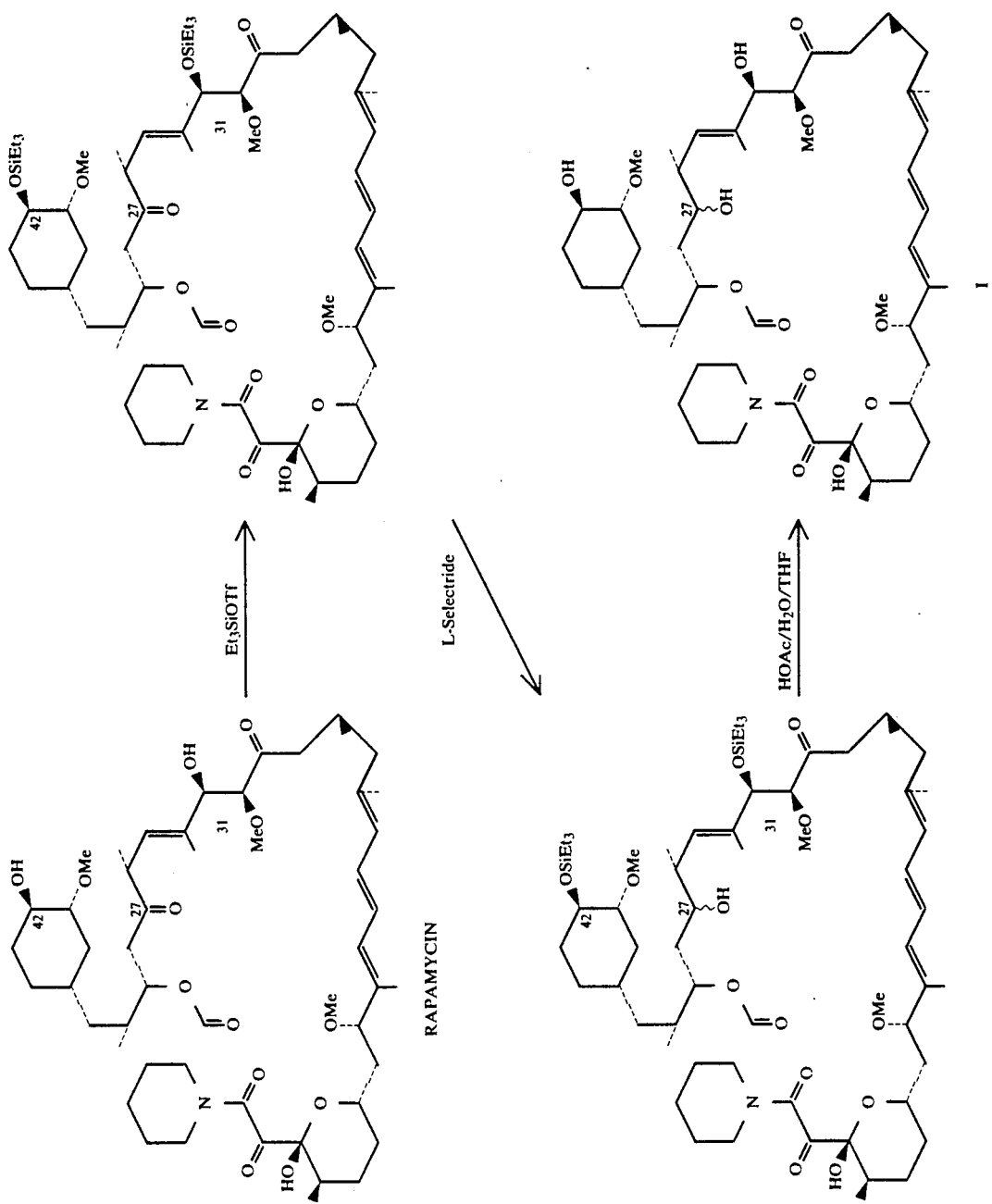

The 31- and 42-hydroxyl groups of rapamycin are first protected with a suitable protecting group, such as the triethylsilyl ether protecting group. Protection of the hydroxyl groups prior to reduction appears to be necessary to prevent overreduction and ring degradation. Reduction of the 27-ketone was selectively accomplished with L-Selectride (lithium tri-sec-butylborohydride) to provide a compound which was named 31,42-bis-triethylsilyl ether of 27-hydroxyrapamycin. Attempted reduction with DIBAL, as disclosed in U.S. Pat. No. 5,102,876, failed to provide any products in which the 27-ketone was the only keto-group that was reduced. Removal of the silyl ether protecting groups was accomplished under mildly acidic conditions, such as with a mixture of acetic acid, water, and THF. Removal of the silyl ether protecting groups can also be accomplished using fluoride ion generating reagents, such as hydrogen fluoride/pyridine. It is also contemplated that the 31- and 42-hydroxyl groups can be protected with other silylating reagants, such as triisopropylsilyl chloride or t-butyldimethylsilyl chloride, to allow selective reduction of the 27-ketone of rapamycin.

The derivatives of 27-hydroxyrapamycin that are claimed as part of this invention can be prepared by reacting the intermediate 31,42-bis-triethylsilyl ether of 27-hydroxyrapamycin with suitable electrophilic agents. The 27-acyl derivatives of formula II can be prepared by the method used in Examples 4 and 5. The 27-acyl derivative of formula II can also be prepared by reacting the 27-hydroxyl group of 31,42-bis-triethylsilyl ether of 27-hydroxyrapamycin with an acylating agent according the method described in U.S. Pat. No. 4,316,885, the disclosure of which is hereby incorporated by reference, followed by deprotection according to Examples 3 or 5.

The 27-fluorinated esters of formula III can be prepared by reacting the 27-hydroxyl group of 31,42-bis-triethylsilyl ether of 27-hydroxyrapamycin with a suitable fluorinated acylating agent as described in U.S. Pat. No. 5,100,883, the disclosure of which is hereby incorporated by reference, followed by deprotection according to Examples 3 or 5.

The 27-amide esters of formula IV can be prepared by acylating the 27-hydroxyl group of 31,42-bis-triethylsilyl ether of 27-hydroxyrapamycin with a suitable acylating agent as described in U.S. Pat. No. 5,118,677, the disclosure of which is hereby incorporated by reference, followed by deprotection according to Examples 3 or 5.

The 27-carbamates of formula V can be prepared by carbamylating the 27-hydroxyl group of 31,42-bis-triethylsilyl ether of 27-hydroxyrapamycin with a suitable carbamylating agent as described in U.S. Pat. No. 5,118,678, the disclosure of which is hereby incorporated by reference, followed by deprotection according to Examples 3 or 5.

The 27-aminoesters of formula VI can be prepared by acylating the 27-hydroxyl group of 31,42-bis-triethylsilyl ether of 27-hydroxyrapamycin with a suitable acylating agent as described in U.S. Pat. No. 5,130,307, the disclosure of which is hereby incorporated by reference, followed by deprotection according to Examples 3 or 5.

The 27-ethers of formula VII can be prepared by reacting the 27-hydroxyl group of 31,42-bis-triethylsilyl ether of 27-hydroxyrapamycin with a suitable acetal forming reagent as described in U.S. Pat. No. 5,151,413, the disclosure of which is hereby incorporated by reference, followed by deprotection using hydrogen fluoride/pyridine according to standard literature procedures. The alkyl or arylalkyl ethers of formula VII can be formed by alkylating the 27-hydroxyl group of 31,42-bis-triethylsilyl ether of 27-hydroxyrapamycin with a suitable alkylating agent, such as with an alkyl halide in pyridine.

The 27-aminoacyl compounds of formula VIII can be prepared by acylating the 27-hydroxyl group of 31,42-bis-triethylsilyl ether of 27-hydroxyrapamycin with a suitable acylating agent as described in U.S. Pat. No. 4,650,803, the disclosure of which is hereby incorporated by reference, followed by deprotection according to Examples 3 or 5.

The 27-sulfonylcarbamates of formula IX can be prepared by carbamylating the 27-hydroxyl group of 31,42-bis-triethylsilyl ether of 27-hydroxyrapamycin with a suitable carbamylating agent as described in U.S. patent application Ser. No. 07/837,048, filed Feb. 18, 1992, the disclosure of which is incorporated by reference, followed by deprotection according to Examples 3 or 5.

The 27-sulfonates and sulfamates of formula X can be prepared by reacting the 27-hydroxyl group of 31,42-bis-triethylsilyl ether of 27-hydroxyrapamycin with a suitable sulfonyl halide or (carboxysulfamoyl)triethylammonium hydroxide inner salt as described in U.S. Pat. No. 5,177,203, the disclosure of which is hereby incorporated by reference, followed by deprotection according to Examples 3 or 5.

Based on this disclosure, other derivatives of 27-hydroxyrapamycin will be apparent to one skilled in the art. For example, it is contemplated that other esters of the 27-hydroxyl group can be prepared. These include both organic esters and inorganic esters, such as phosphate, nitrate, sulfinate, sulfonate esters, and the like, and organic esters of these inorganic acids. These compounds are also expected to have a similar activity profile to the compounds of this invention. Additionally, the 27-hydroxyl group may be protected with suitable protecting groups, such as a silyl ether, to provide a 27,31,42-tris-silyl ether of 27-hydroxyrapamycin.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours Cells are cultured with and without various concentrations of rapamycin, cyclosporin A, or test compound. Cells are harvested and incorporated radioactivity is determined. Inhibition of lymphoproliferation is assessed as percent change in counts per minute from nondrug treated controls. The results are expressed as an $IC_{50}$.

A representative compound of this invention was also evaluated in an in vivo test procedure designed to determine the survival time of pinch skin graft from male DBA/2 donors transplanted to male BALB/c recipients. The method is adapted from Billingham R. E. and Medawar P. B., J. Exp. Biol. 28:385-402, (1951).

Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ±S.D.) of the drug treatment group is compared with the control group.

The following table summarizes the results of representative compounds of this invention in these three standard test procedures.

TABLE 1

| Compound | LAF ($IC_{50}$) | Skin Graft (days ± SD) |
|---|---|---|
| 27-Hydroxyrapamycin | 3.7 nM | 8.5 ± 1.2* |
| | | 8.17 ± 0.75* |
| | | 8.00 ± 0.63* |
| | | 9.17 ± 0.98+ |
| | | 9.17 ± 0.75+ |
| Example 5 | 99 nM# | |
| Rapamycin | 4.8 nM | 12.0 ± 1.7* |
| No Treatment | | 7.2 ± 0.45 |

*Evaluated in the skin graft procedure at a dose of 4 mg/kg.
+Evaluated in the skin graft procedure at a dose of 16 mg/kg.
94% inhibition of T-cell proliferation at 1 µM and 69% inhibition at 0.1 µM.

The results of these standard pharmacological test procedures demonstrate immunosuppressive activity both in vitro and in vivo for the compounds of this invention. The results obtained in the LAF test procedure indicates suppression of T-cell proliferation. As a transplanted pinch skin grafts are typically rejected within 6–7 days without the use of an immunosuppressive agent, the increased survival time of the skin graft when treated with the compounds of this invention further demonstrates their utility as immunosuppressive agents.

Because the compounds of this invention are structurally similar to rapamycin and have a similar activity profile to rapamycin, the compounds of this invention also are considered to have antitumor, antifungal, and antiproliferative activities.

As such, the compounds of this invention are useful in the treatment of transplantation rejection such as, heart, kidney, liver, bone marrow, and skin transplants; autoimmune diseases such as lupus, rheumatoid arthritis, diabetes mellitus, myasthenia gravis, and multiple sclerosis; diseases of inflammation such as psoriasis, dermatitis, eczema, seborrhea, inflammatory bowel disease, and eye uveitis; solid tumors; fungal infections; and hyperproliferative vascular diseases such as restenosis.

Additionally, 27-Hydroxyrapamycin was found to have a half life of 17.5 hours in 0.1M phosphate buffer (pH 7.4, 37° C.) whereas rapamycin was found to have a half life of 11.8 hours under the same conditions. Therefore, by virtue of the reduced ketone at the 27-position, 27-hydroxyrapamycin provides an advantage over rapamycin by preventing degredative ring opening reactions, thus resulting in a more stable compound. The 27-hydroxyrapamycin derivatives of formulas II–X are also expected to resist ring degredative reactions better than rapamycin and 31- and/or 42-substituted rapamycin derivatives of rapamycin. The half life of 27-hydroxyrapamycin-27-ester with acetic acid in 0.1M phosphate buffer (pH 7.4, 37° C.) is 34 hours.

As 27-hydroxyrapamycin and the compound of Example V was prepared via its 31,42-silylated intermediate (Example 2), the compound of Example 2 is therefore useful as an intermediate of these two compounds. Additionally, 31,42-Bis-triethylsilyl ether of 27-hydroxyrapamycin-27-ester with acetic acid is also a useful intermediate in the preparation of the compound of Example 5.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally in the form of a conventional suppository.

For administration by intranasal or intrabronchial inhalation or insulflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily intravenous dosages of the compounds of this invention would be 0.001-25 mg/kg, preferably between 0.005-5 mg/kg, and more preferably between 0.01-0.5 mg/kg. Projected daily oral dosages of the compounds of this invention would be 0.005-75 mg/kg, preferably between 0.01-50 mg/kg, and more preferably between 0.05-10 mg/kg.

Treatment will generally be initiated with small dosages less than the optimum dose of the compound. Thereafter the dosage is increased until the optimum effect under the circumstances is reached; precise dosages for oral, parenteral, intranasal, intrabronchial, transdermal, or rectal administration will be determined by the administering physician based on experience with the individual subject treated. In general, the compounds of this invention, are most desirably administered at a concentration that will generally afford effective results without causing any harmful or deleterious side effects.

The following examples illustrate the preparation of representative compounds of this invention.

EXAMPLE 1

31,42-Bis-triethylsilyl ether of rapamycin

To a solution of rapamycin (2 g, 2.18 mmol) in $CH_2Cl_2$ (10.9 mL) at 0° C. was added 2,6-lutidine (1.17 mL, 10.1 mmol) and triethylsilyl trifluoromethanesulfonate (1.13 mL, 5.03 mmol) dropwise. The reaction was stirred at 0° C. for an additional 45 min, allowed to warm to room temperature, and stirred overnight. The reaction was then quenched with $NaHCO_3$ and diluted with ethyl acetate. The organic layer was separated and washed with 2N HCl, $NaHCO_3$, brine, dried over $Na_2SO_4$, and concentrated in vacuo. The residue was chromatographed using hexane-ethyl acetate (4:1) as eluant to provide 1.04 g (42%) of 31,42-bis-triethylsilyl ether of rapamycin.

IR (KBr) 3500 (m, br), 2925 (s), 2875 (s), 1720 (s), 1640 (s), 1450 (s), 1370 (w), 1235 (w), 1185 (w), 1100 (s), 980 (m), 815 (m), 745 (m); $^1$H NMR (400 MHz, $CDCl_3$) δ0.44-0.50 (comp m, 6H), 0.52-0.60 (comp m, 6H), 0.67 (m, 1H), 0.82-0.96 (comp m, 24H), 1.00-1.04 (comp m, 9H), 1.06-1.25 (comp m, 4H), 1.30-1.60 (comp m, 12H), 1.61, 1.64 (d, rotamers, J=3.74, 0.80 Hz, 3H), 1.68-1.83 (comp m, 5H), 1.72, 1.74 (d, rotamers, J=1.04 Hz, 3H), 1.96 (m, 1H), 2.25 (m, 2H), 2.32 (dd, J=3.00, 15.88 Hz, 1H), 2.58 (dd, J=8.09, 16.00 Hz, 1H), 2.68 (m, 1H), 2.87 (m, 1H), 3.10, 3.11 (s, rotamers, 3H), 3.24 (s, 3H), 3.33 (m, 3H), 3.37, 3.39 (s, rotamers, 3H), 3.68 (m, 2H), 3.75 (m, 1H), 3.82 (d, J=6.23 Hz, 1H), 4.10 (d, J=5.60 Hz, 1H), 4.68 (d, J=1.66 Hz, 1H), 5.00 (m, 1H), 5.20 (d, J=10.17 Hz, 1H), 5.28 (d, J=4.57 Hz, 1H), 5.53 (dd, J=8.20, 15.05 Hz, 1H), 6.02 (dd, J=1.04, 10.79 Hz, 1H), 6.14 (m, 1H), 6.34 (qd, J=10.48, 28.94 Hz, 2H); $^{13}$C NMR (100 MHz, $CDCl_3$) δ4.63, 4.72, 5.01, 6.68, 6.72, 6.79, 10.14, 12.33, 13.72, 14.94, 15.42, 16.06, 21.46, 25.14, 26.86, 27.31, 31.29, 31.82, 32.97, 33.88, 33.98, 34.08, 35.24, 36.15, 38.60, 38.67, 39.87, 41.70, 42.44, 44.03, 47.03, 51.25, 55.78, 58.07, 58.15, 66.92, 75.61, 79.26, 84.05, 84.11, 84.80, 98.67, 126.81, 127.12, 129.36, 130.68, 132.85, 135.84, 138.16, 139.18, 166.29, 169.61, 193.41, 208.34, 211.46; high resolution mass spectrum (negative ion FAB) m/z 1141.7 [(M-H); calcd for $C_{63}H_{106}NO_{13}Si_2$: 1141.6].

EXAMPLE 2

31,42-Bis-triethylsilyl ether of 27-hydroxyrapamycin

To a solution of 31,42-bis-triethylsilyl ether of rapamycin (400 mg, 0.35 mmol) in THF (3.5 mL) at −78° C. was added L-Selectride (0.4 mL, 0.4 mmol, 1M in THF) dropwise. After 2 h, the reaction was quenched with $H_2O$ and EtOAc and allowed to warm to room temperature. The aqueous layer was separated and extracted with EtOAc. The organic layers were combined, washed with brine, dried over $Na_2SO_4$ and concentrated in vacuo. The residue was purified via flash column chromatography using hexane-ethyl acetate (3:1) as eluant to provide 140 mg (35%) of 31,42-bis-triethylsilyl ether of 27-hydroxyrapamycin.

IR (KBr) 3300 (s, br), 2950 (s), 2880 (s), 1720 (s), 1640 (s), 1450 (s), 1190 (w), 1100 (s), 1010 (m), 800 (m), 749 (m); $^1$H NMR (400 MHz, $CDCl_3$) δ0.47 (m, 6H), 0.49 (m, 6H), 0.57 (m, 1H), 0.81-1.00 (comp m, 27H), 1.01-1.04 (comp m, 6H), 1.14-1.58 (comp m, 16H), 1.60 (d, J=0.83 Hz, 3H), 1.63 (d, J=0.83 Hz, 3H), 1.64-1.82 (comp m, 8H), 2.00 (m, 2H), 2.31 (m, 2H), 2.43 (m, 1H), 2.78 (m, 1H), 2.88 (m, 1H), 3.11 (s, 3H), 3.21, 3.23 (s, rotamers, 3H), 3.37 (m, 3H), 3.40, 3.41 (s, rotamers, 3H), 3.54 (m, 1H), 3.70 (m, 1H), 3.73 (d, J=7.26 Hz, 1H), 3.78 (m, 1H), 4.06 (d, J=7.06 Hz, 1H), 4.81 (s, 1H), 5.02 (m, 1H), 5.23 (d, J=8.72 Hz, 1H), 5.33 (dd, J=0.42, 4.78 Hz, 1H), 5.66 (dd, J=7.15, 15.04 Hz, 1H), 6.00 (d, J=9.75 Hz, 1H), 6.13 (m, 1H), 6.30 (m, 2H); $^{13}$C NMR (100 MHz, $CDCl_3$) δ4.69, 4.99, 5.03, 6.74, 6.82, 10.03, 12.12, 13.78, 14.14, 15.42, 16.16, 20.89, 21.38, 25.37, 27.06, 27.36, 29.69, 31.25, 31.86, 33.20, 33.86, 34.07, 34.15, 34.70, 36.17, 36.37, 38.70, 38.74, 39.71, 42.61, 44.21, 51.17, 55.79, 58.15, 58.22, 67.07, 71.59, 75.70, 79.23, 84.23, 84.85, 98.44, 126.78, 129.51, 130.11, 131.12, 133.31, 135.40, 136.02, 139.27, 167.00, 169.73, 192.86, 212.62; high resolution mass spectrum (negative ion FAB) m/z 1143.7 [(M-H); calcd for $C_{63}H_{108}NO_{13}Si_2$: 1143.6].

EXAMPLE 3

27-Hydroxyrapamycin 31,42-Bis-triethylsilyl ether of 27-hydroxyrapamycin (101 mg, 0.088 mmol) was dissolved in 1.5 mL of HOAc:THF:H₂O (3:1:1). Additional THF (0.1 mL) was added to effect solution. The reaction was stirred overnight and then diluted with ethyl acetate and washed with NaHCO₃. The aqueous layer was back extracted with ethyl acetate. The organic layers were combined, washed with brine, dried over Na₂SO₄, and concentrated in vacuo. The residue was purified via flash column chromatography using CHCl₃:MeOH (95:5) as eluant to provide 57 mg (70%) of 27-Hydroxyrapamycin.

IR (KBr) 3440 (s, br), 2920 (s), 1740 (s), 1650 (s), 1440 (s), 1370 (w), 1190 (w), 1085 (m), 985 (m); $^1$H NMR (400 MHz, CDCl₃) δ0.68 (m, 1H), 0.83–1.08 (comp m, 15H), 1.16–1.62 (comp m, 12H), 1.66 (s, 3H), 1.68 (s, 3H), 1.71–1.88 (comp m, 8H), 1.98 (m, 2H), 2.14 (m, 3H), 2.28 (m, 2H), 2.39 (m, 1H), 2.66 (s, 1H), 2.84 (m, 1H), 2.94 (m, 1H), 3.13 (s, 3H), 3.28 (d, J=1.18 Hz, 1H), 3.34 (s, 3H), 3.42 (s, 3H), 3.47–3.58 (comp m, 3H), 3.58 (d, J=7.24 Hz, 1H), 3.65 (m, 1H), 3.81 (m, 1H), 4.13 (m, 1H), 4.84 (s, 1H), 4.99 (m, 1H), 5.31 (m, 2H), 5.55 (dd, J=9.0, 24.0 Hz, 1H), 5.94 (d, J=10.5 Hz, 1H), 6.15 (m, 1H), 6.35 (m, 2H); $^{13}$C NMR (100 MHz, CDCl₃) δ10.09, 12.52, 14.03, 15.67, 16.16, 16.22, 20.56, 21.93, 25.27, 26.94, 27.22, 31.22, 31.27, 31.89, 33.22, 33.31, 33.62, 34.00, 35.37, 35.46, 37.99, 38.77, 38.82, 39.03, 40.09, 40.92, 44.22, 51.33, 55.82, 56.62, 60.03, 67.17, 73.65, 73.92, 78.06, 78.89, 84.46, 85.17, 98.42, 126.25, 129.80, 130.31, 131.01, 133.20, 133.73, 135.16, 140.43, 167.06, 170.14, 192.39, 217.19; high resolution mass spectrum (negative ion FAB) m/z 915.3 [(M-H); calcd for $C_{57}H_{80}NO_{13}$: 915.2].

EXAMPLE 4

31,42-Bis-triethylsilyl ether of 27-hydroxyrapamycin-27-ester with acetic acid To a solution of 31,42-bis-triethylsilyl ether of 27-hydroxyrapamycin (0.74 g, 0.64 mmol) in CH₂Cl₂ (3.2 mL) at 0° C. was added pyridine (0.2 mL, 2.58 mmol) and acetyl chloride (0.092 mL, 1.29 mmol) dropwise. The reaction was held at 0° C. for 30 min, allowed to warm to room temperature, and stirred for 3 h. Additional equivalents of pyridine (0.050 mL, 0.61 mmol) and acetyl chloride (0.023 mL, 0.32 mmol) were added at 0° C. The reaction was again allowed to warm to room temperature and was quenched after an additional 1.5 h with NaHCO₃ and diluted with ethyl acetate. The organic layer was separated and washed with 1N HCl, NaHCO₃, brine, dried over Na₂SO₄, and concentrated in vacuo. The residue was chromatographed using hexane-ethyl acetate (4:1) as eluant to provide 0.237 g (31%) of 31,42-bis-triethylsilyl ether-27-hydroxyrapamycin-27-ester with acetic acid along with 0.154 g (20%) of recovered starting material.

IR (KBr) 3400 (w, br), 2940 (s), 1740 (s), 1650 (m), 1460 (m), 1240 (s), 1105 (s), 1005 (w), 740 (m); $^1$H NMR (400 MHz, CDCl₃) δ0.46–0.54 (comp m, 6H), 0.57–0.63 (comp m, 6H), 0.75 (m, 1H), 0.81–0.99 (comp m, 27H), 1.05 (m, 6H), 1.54 (s, 3H), 1.22–1.63 (comp m, 16H), 1.64 (d, J=1.8 Hz, 3H), 1.66–1.98 (comp m, 8H), 1.99 (s, 3H), 2.06 (m, 1H), 2.32 (m, 2H), 2.62 (m, 1H), 2.78 (m, 1H), 2.89 (m, 1H), 3.14 (s, 3H), 3.23 (s, 3H), 3.42 (m, 2H), 3.43 (s, 3H), 3.54 (m, 1H), 3.75 (d, superimposed on m, J=7.2 Hz, 1H), 3.76 (m, 2H), 4.08 (d, J=6.7 Hz, 1H), 4.87 (dd, J=0.41, 4.98 Hz, 1H), 4.99 (m, 1H), 5.03 (m, 1H), 5.20 (d, J=0.4 Hz, 1H), 5.41 (m, 1H), 5.78 (m, 1H), 6.00 (m, 1H), 6.13 (m, 1H), 6.37 (m, 2H); $^{13}$C NMR (100 MHz, CDCl₃) δ4.6, 4.9, 6.7, 6.8, 9.9, 14.0, 14.9, 15.3, 16.2, 20.6, 20.8, 20.9, 25.4, 27.3, 27.4, 30.1, 31.3, 31.7, 33.1, 33.3, 33.5, 33.9, 34.0, 34.2, 36.2, 38.2, 38.6, 39.9, 42.6, 44.0, 50.8, 55.6, 58.0, 58.3, 66.9, 73.7, 75.6, 75.9, 76.4, 79.1, 84.1, 84.4, 98.2, 126.6, 129.6, 129.9, 130.0, 133.6, 134.5, 135.9, 139.0, 167.1, 169.3, 170.5, 191.6, 212.0; high resolution mass spectrum (negative ion FAB) m/z 1185.7 [(M-H); calcd for $C_{65}H_{110}NO_{14}Si_2$: 1185.6].

EXAMPLE 5

27-Hydroxyrapamycin-27-ester with acetic acid 31,42-bis-triethylsilyl ether-27-hydroxyrapamycin-27-ester with acetic acid (0.16 g, 0.13 mmol) was dissolved in 2.5 mL of a 3:1:1 solution of HOAc:THF:H₂O. The reaction was stirred overnight and was then quenched with NaHCO₃ and diluted with ethyl acetate. The organic layer was separated and washed with NaHCO₃, brine, dried over Na₂SO₄, and concentrated in vacuo. The residue was chromatographed using CH₂Cl₂:MeOH (20:1) as eluant followed by HPLC (70:30 hexane:ethyl acetate gradient over 60 min to 100% ethyl acetate) to provide 0.050 g (40%) of 27-hydroxyrapamycin-27-ester with acetic acid.

$^1$H NMR (400 MHz, CDCl₃) δ0.68 (m, 1H), 0.95–1.04 (comp m, 15H), 1.13–1.69 (comp m, 18H), 1.59 (s, 3H), 1.66 (d, J=5.6 Hz, 3H), 1.78–1.98 (comp m, 9H), 2.02 (s, 3H), 2.30 (m, 2H), 2.68 (m, 1H), 2.85 (m, 1H), 2.95 (m, 1H), 3.13 (s, 3H), 3.37 (s, 3H), 3.43 (s, superimposed on m, 3H), 3.43 (m, 2H), 3.59–3.70 (comp m, 3H), 3.79 (m, 1H), 4.09 (d, J=7.9 Hz, 1H), 4.80 (m, 2H), 5.17 (s, 1H), 5.25 (d, J=10.0 Hz, 1H), 5.35 (d, J=5.3 Hz, 1H), 5.76 (dd, J=8.9, 19.8 Hz, 1H), 5.90 (d, J=9.1 Hz, 1H), 6.14 (m, 1H), 6.36 (m, 2H); high resolution mass spectrum (negative ion FAB) m/z 957.2 [(M-H); calcd for $C_{53}H_{82}NO_{14}$: 957.5].

Anal. Calcd for $C_{53}H_{83}NO_{14}$•0.1Et₂O: C, 65.9 H, 8.66 N, 1.45. Found: C, 65.9 H, 8.72 N, 1.34.

The following representative compounds or pharmaceutically acceptable salts thereof could be readily prepared based on the methodology described in this disclosure.

27-Hydroxyrapamycin-27-ester with benzoic acid
27-Hydroxyrapamycin-27-ester with phenylacetic acid
27-Hydroxyrapamycin-27-ester with pyridine-2-carboxylic acid
27-Hydroxyrapamycin-27-ester with trifluoroacetic acid
27-Hydroxyrapamycin-27-ester with 3,3,3-trifluoropropanoic acid
27-Hydroxyrapamycin-27-ester with difluoroacetic acid
27-Hydroxyrapamycin-27-ester with pentafluoropropionic acid
27-Hydroxyrapamycin-27-ester with 4-(dimethylamino)-4-oxobutanoic acid
27-Hydroxyrapamycin-27-ester with 4-oxo-4-[[2-(2-pyridinyl)ethyl]amino]butanoic acid
27-Hydroxyrapamycin-27-ester with 2-[2-[(3-carboxy-1-oxopropyl)amino]ethyl]-1-methyl-pyridinium iodide
27-Hydroxyrapamycin-27-ester with (4-fluorophenyl)-carbamic acid
27-Hydroxyrapamycin-27-ester with phenylcarbamic acid
27-Hydroxyrapamycin-27-ester with 4-[(trifluoromethyl)phenyl]carbamic acid
27-Hydroxyrapamycin-27-ester with (4-nitrophenyl)-carbamic acid
27-Hydroxyrapamycin-27-ester with (4-methylphenyl)carbamic acid 27-Hydroxyrapamycin-27-ester with (2,4-difluorophenyl)carbamic acid 27-Hydroxyrapamycin-27-ester with N-[(1,1-dimethylethoxy)carbonyl]-glycylglycine 27-Hydroxyrapamycin-27-ester with N-[(1,1-dimethylethoxy)carbonyl]-N-methylglycine 27-Hydroxyrapamycin-27-ester with 5-(1,1-dimethylethoxy)-2-[[(1,1-dimethylethoxy)carbonyl]amino]-5-oxopentanoic acid 27-Hydroxyrapamycin-27-ester with 2-[[(1,1-dimethylethoxy)carbonyl]amino]-4-oxo-4-(phenylmethoxy)-butanoic acid 27-Hydroxyrapamycin-27-ester with 3-[[(1,1-dimethylethoxy)carbonyl]amino]-4-oxo-4-(phenylmethoxy)-butanoic acid 27-Hydroxyrapamycin-27-ester with 5-(1,1-dimethyloxy)-4-[[(1,1-dimethylethoxy)carbonyl]amino]-5-oxopentanoic acid 27-Hydroxyrapamycin-27-ester with $N^\alpha$, $N^\epsilon$-bis[(1,1-dimethylethoxy)carbonyl]-L-lysine 27-Hydroxyrapamycin-27-ether with (1-methoxy-1-methyl)ethanol 27-Hydroxyrapamycin-27-ether with (2-(trimethylsilyl)ethoxy)methanol 27-Hydroxyrapamycin-27-ester with N,N-dimethylglycine 27-Hydroxyrapamycin-27-ester with 3-(N,N-diethylamino)propionic acid 27-Hydroxyrapamycin-27-ester with 4'-(N-pyrrolidino)butyric acid 27-Hydroxyrapamycin-27-ester with phenylsulfonylcarbamic acid 27-Hydroxyrapamycin-27-ester with (4-chlorophenylsulfonyl)carbamic acid 27-Hydroxyrapamycin-27-ester with (3-methylphenylsulfonyl)carbamic acid 27-Hydroxyrapamycin-27-ester with 5-(dimethylamino)-1-naphthalensulfonic acid 27-Hydroxyrapamycin-27-ester with 4-methylbenzenesulfonic acid 27-Hydroxyrapamycin-27-ester with 2-thiophenesulfonic acid 27-Hydroxyrapamycin-27-ester with 4-[[4-(dimethylamino)phenyl]aza]benzenesulfonic acid 27-Hydroxyrapamycin-27-ester with 1-naphthalenesulfonic acid 27-Hydroxyrapamycin-27-ester with 8-quinolinsulfonic acid 27-Hydroxyrapamycin-27-ester with methanesulfonic acid 27-Hydroxyrapamycin-27-ester with 2,2,2-trifluoroethanesulfonic acid 27-Hydroxyrapamycin-27-ester with [(methoxycarbonyl)amino]sulfonic acid

What is claimed is:

1. A compound of the formula

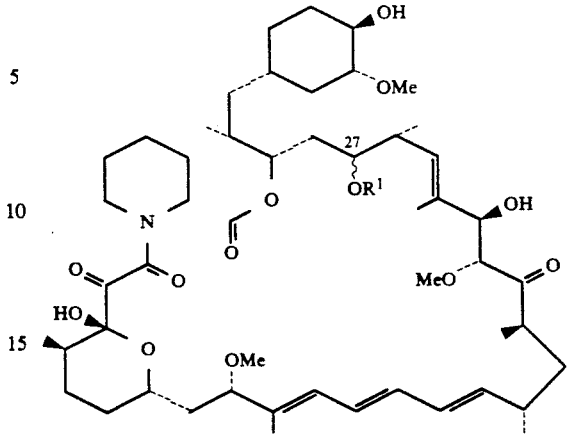

wherein
$R^1$ is

and $R^2$ is alkyl of 1–10 carbon atoms, arylalkyl of 7–10 carbon atoms, or aryl wherein the aryl group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H;

or a pharmaceutically acceptable salt thereof.

2. A compound of claim 1 which is 27-hydroxyrapamycin-27-ester with acetic acid.

3. A compound of the formula

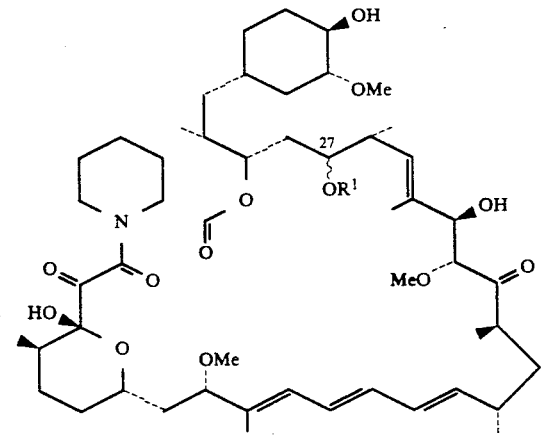

wherein
$R^1$ is

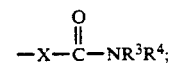

and

R² is a mono-, di-, poly-, or per-fluorinated alkyl group of 1-10 carbon atoms.

4. A compound of the formula

wherein
R¹ is

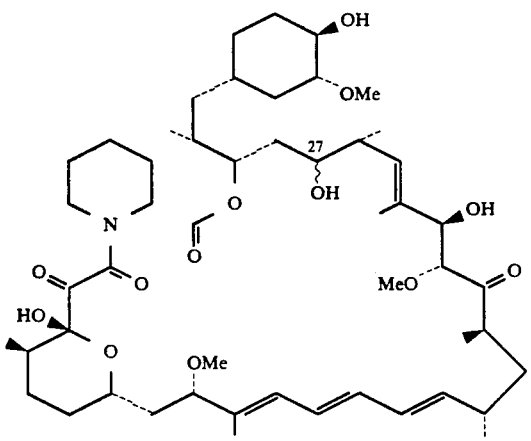

R² is

X is —(CH$_2$)$_m$— or —Ar—;

R³ and R⁴ are each, independently, hydrogen, alkyl of 1-12 carbon atoms, —(CH$_2$)$_n$—Ar, —(CH$_2$)$_p$—NR⁵R⁶, or —(CH$_2$)$_p$—N+R⁵R⁶R⁷Y−;

R⁵ and R⁶ are each, independently, hydrogen, alkyl of 1-12 carbon atoms, or —(CH$_2$)$_n$—Ar;

Ar is an optionally mono- or di-substituted group selected from

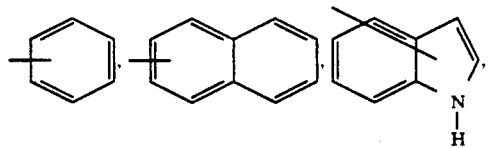

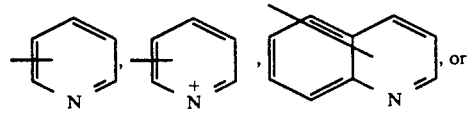

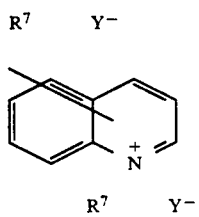

in which the optional substituents are selected from the group consisting of alkyl of 1-6 carbon atoms, arylalkyl of 7-10 carbon atoms, alkoxy of 1-6 carbon atoms, cyano, halo, nitro, carbalkoxy of 2-7 carbon atoms, or perfluoroalkyl of 1-6 carbon atoms;

R⁷ is alkyl of 1-6 carbon atoms;

Y is a halide, sulfate, phosphate, or p-toluenesulfonate anion;

m = 1-6;
n = 1-6;
p = 1-6;

or a pharmaceutically acceptable salt thereof.

5. A compound of the formula

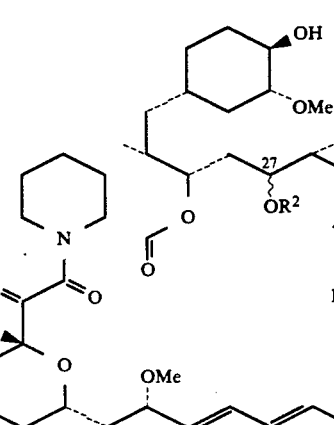

wherein
R² is

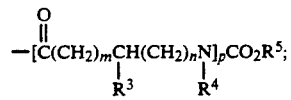

R³ is hydrogen, alkyl of 1-6 carbon atoms, arylalkyl of 7-10 carbon atoms, —(CH$_2$)$_q$CO$_2$R⁶, —(CH$_2$)$_r$NR⁷CO$_2$R⁸, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

R⁴ and R⁷ are each, independently, hydrogen, alkyl of 1-6 carbon atoms, or arylalkyl of 7-10 carbon atoms;

R⁵, R⁶, and R⁸ are each, independently, alkyl of 1-6 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

m is 0-4;
n is 0-4;
p is 1-2;
q is 0-4;
r is 0-4;

wherein $R^3$, $R^4$, m, and n are independent in each of the

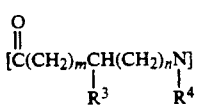

subunits when p=2;
or a pharmaceutically acceptable salt thereof.

6. A compound of the formula

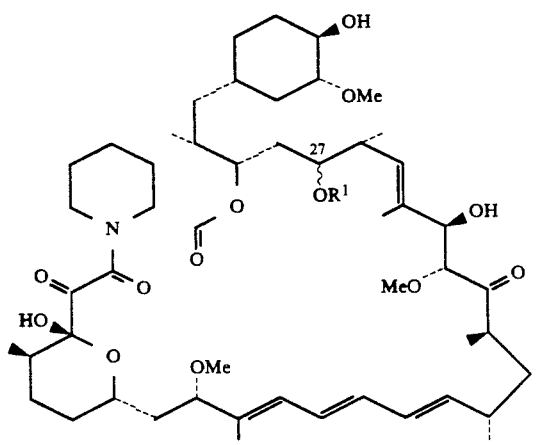

VII wherein
$R^1$ is alkyl of 1-6 carbon atoms, arylalkyl of 7-10 carbon atoms, —CH₂YX, —C(CH₃)₂YX, —CH(CH₃)YX, or L;
Y is O or S;
X is —CH₃, —(CH₂)$_n$CH₃, —CH₂Ar, —(CH₂)₂OCH₃, —CH₂CCl₃, —CH(CH₃)₂, or —CH₂CH₂SiMe₃;
L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S dioxide; and
n=1-5.

7. A compound of the formula

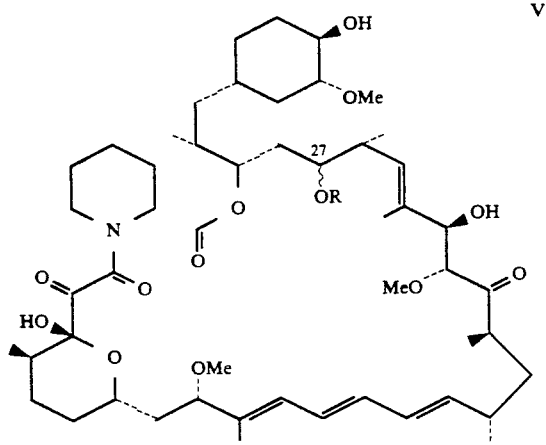

VIII wherein
R is

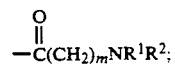

$R^1$ and $R^2$ are each hydrogen or alkyl of 1-3 carbon atoms or $R^1$ and $R^2$ together with the nitrogen to which they are attached form a saturated heterocyclic ring having 4-5 carbon atoms; and
m=1-3 or a pharmaceutically acceptable salt thereof.

8. A compound of the formula

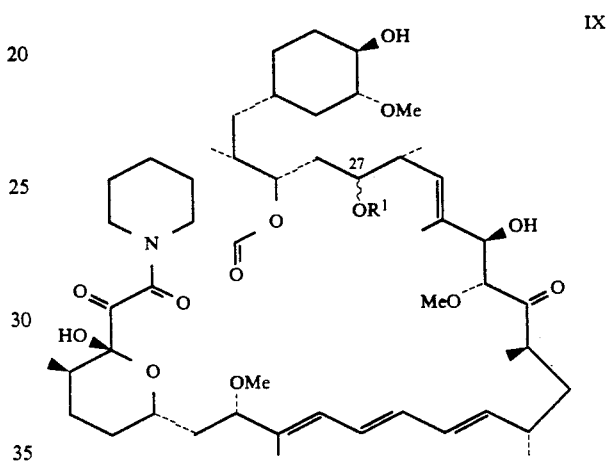

IX wherein
$R^1$ is —CONHSO₂—Ar; and
Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;

or a pharmaceutically acceptable salt thereof when the Ar group contains a basic nitrogen or when the Ar group is substituted by dialklyamino of 1-6 carbon atoms per alkyl group, —SO₃H, —PO₃H, or —CO₂H;

or a pharmaceutically acceptable salt thereof.

9. A compound of the formula

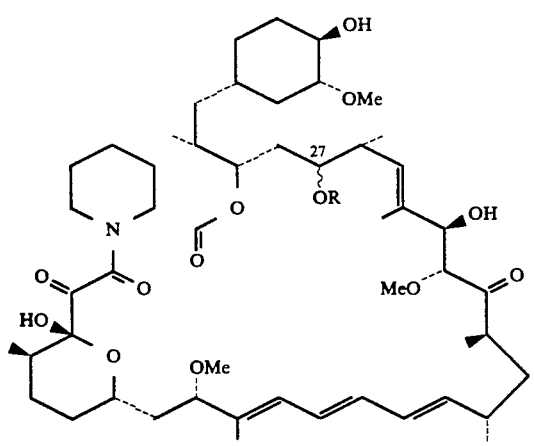

wherein
R is —SO$_2$R$^1$;
R$^1$ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR$^2$; and
R$^2$ is lower alkyl containing 1 to 6 carbon atoms;
or a pharmaceutically acceptable salt thereof.

10. A method of inducing immunosuppression which comprises administering an immunosuppressive effective amount of a compound of formula II,

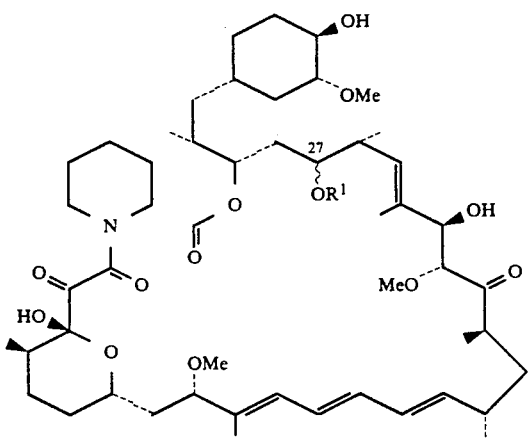

wherein
R$^1$ is

and
R$^2$ is alkyl of 1-10 carbon atoms, arylalkyl of 7-10 carbon atoms, or aryl wherein the aryl group may be optionally mono-, di-, or tri- substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;
or a pharmaceutically acceptable salt thereof;
or of formula III,

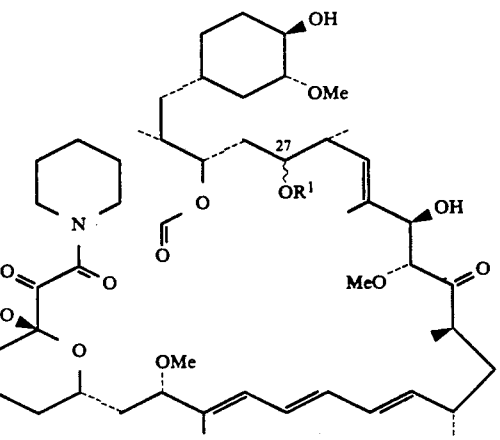

wherein
R$^1$ is

and
R$^2$ is a mono-, di-, poly-, or per-fluorinated alkyl group of 1-10 carbon atoms;
or of formula IV,

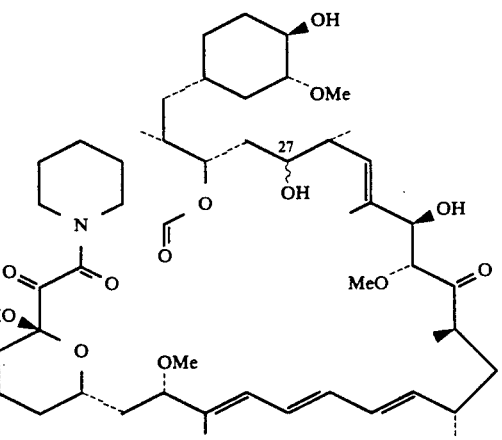

wherein
R$^1$ is

R$^2$ is

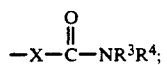

X is —(CH$_2$)$_m$— or —Ar—;

$R^3$ and $R^4$ are each, independently, hydrogen, alkyl of 1-12 carbon atoms, —(CH$_2$)$_n$—Ar, —(CH$_2$)$_p$—NR$^5$R$^6$, or —(CH$_2$)$_p$—N$^+$R$^5$R$^6$R$^7$Y$^-$;

$R^5$ and $R^6$ are each, independently, hydrogen, alkyl of 1-12 carbon atoms, or —(CH$_2$)$_n$—Ar;

Ar is an optionally mono- or di- substituted group selected from

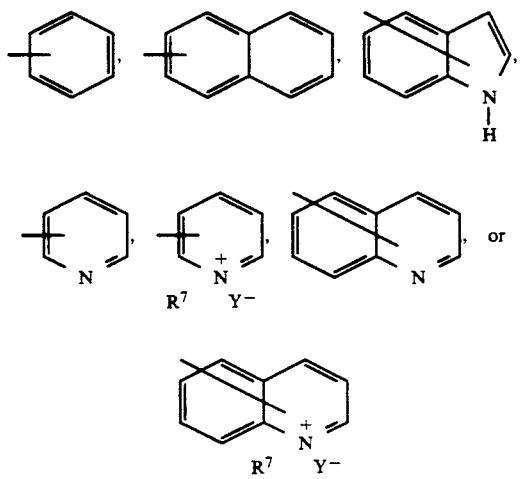

in which the optional substituents are selected from the group consisting of alkyl of 1-6 carbon atoms, arylalkyl of 7-10 carbon atoms, alkoxy of 1-6 carbon atoms, cyano, halo, nitro, carbalkoxy of 2-7 carbon atoms, or perfluoroalkyl of 1-6 carbon atoms;

$R^7$ is alkyl of 1-6 carbon atoms;

Y is a halide, sulfate, phosphate, or p-toluenesulfonate anion;

m=1-6;
n=1-6;
p=1-6;

or a pharmaceutically acceptable salt thereof;
or of formula VI,

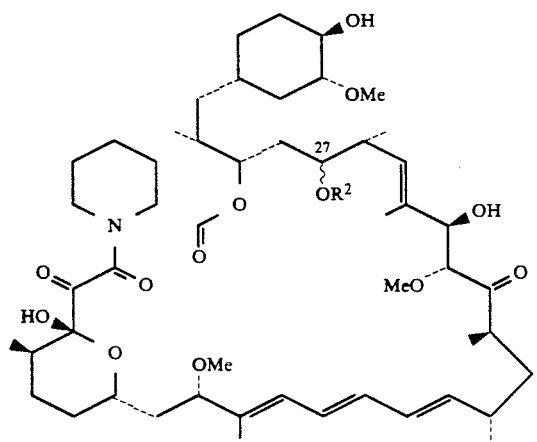

wherein
$R^2$ is

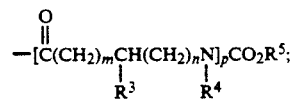

$R^3$ is hydrogen, alkyl of 1-6 carbon atoms, arylalkyl of 7-10 carbon atoms, —(CH$_2$)$_q$CO$_2$R$^6$, —(CH$_2$)$_r$NR$^7$CO$_2$R$^8$, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

$R^4$ and $R^7$ are each, independently, hydrogen, alkyl of 1-6 carbon atoms, or arylalkyl of 7-10 carbon atoms;

$R^5$, $R^6$, and $R^8$ are each, independently, alkyl of 1-6 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

m is 0-4;
n is 0-4;
p is 1-2;
q is 0-4;
r is 0-4;
wherein
$R^3$, $R^4$, m, and n are independent in each of the

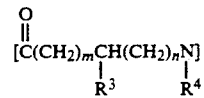

subunits when p=2;
or a pharmaceutically acceptable salt thereof;
or of formula VII,

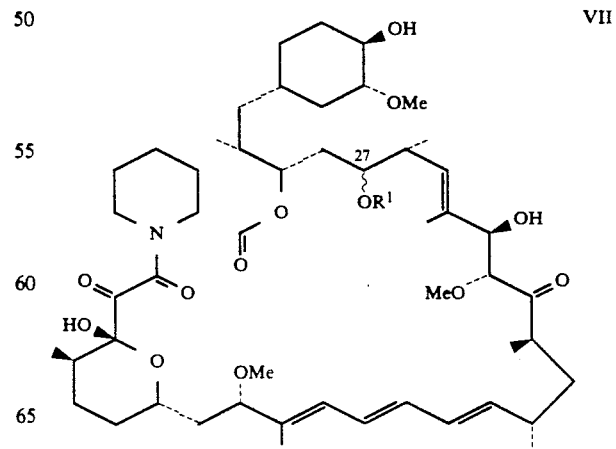

wherein $R^1$ is alkyl of 1–6 carbon atoms, arylalkyl of 7–10 carbon atoms, —CH$_2$YX, —C(CH$_3$)$_2$YX, —CH(CH$_3$)YX, or L;

Y is O or S;

X is —CH$_3$, —(CH$_2$)$_n$CH$_3$, —CH$_2$Ar, —(CH$_2$)$_2$OCH$_3$, —CH$_2$CCl$_3$, —CH(CH$_3$)$_2$, or —CH$_2$CH$_2$SiMe$_3$;

L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S dioxide; and n = 1–5;

or of formula VIII,

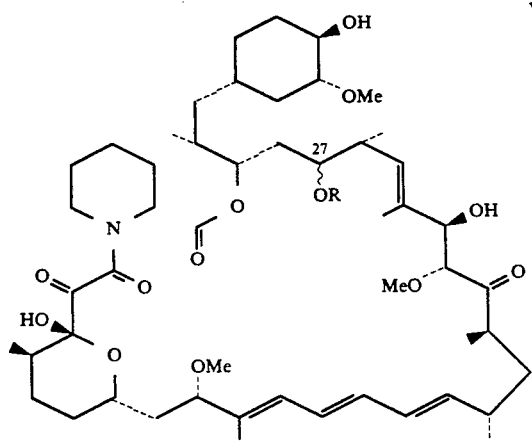

wherein
R is

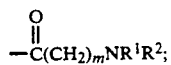

$R^1$ and $R^2$ are each hydrogen or alkyl of 1–3 carbon atoms or $R^1$ and $R^2$ together with the nitrogen to which they are attached form a saturated heterocyclic ring having 4–5 carbon atoms; and m = 1–3 or a pharmaceutically acceptable salt thereof;

or of formula IX,

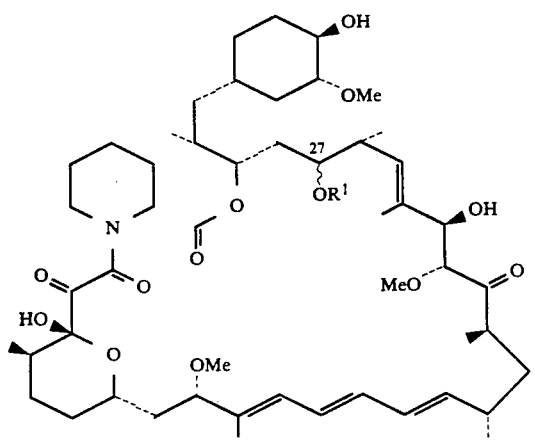

wherein
$R^1$ is —CONHSO$_2$—Ar; and

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H;

or a pharmaceutically acceptable salt thereof when the Ar group contains a basic nitrogen or when the Ar group is substituted by dialkylamino of 1–6 carbon atoms per alkyl group, —SO$_3$H, —PO$_3$H, or —CO$_2$H;

or a pharmaceutically acceptable salt thereof;

or of formula X,

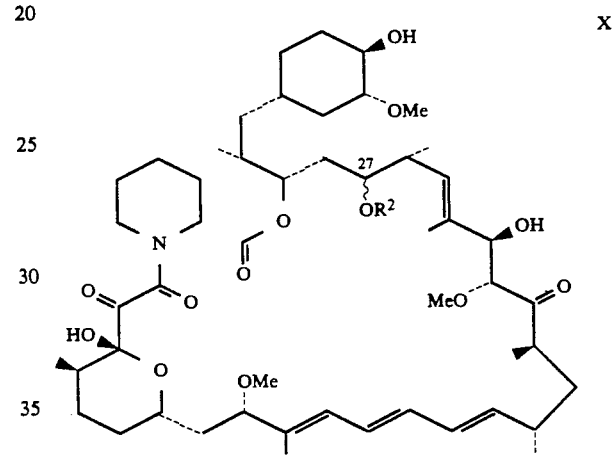

wherein
R is —SO$_2$R$^1$;

$R^1$ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR$^2$; and $R^2$ is lower alkyl containing 1 to 6 carbon atoms;

or a pharmaceutically acceptable salt thereof.

11. A pharmaceutical composition which comprises an effective amount of a compound of formula II,

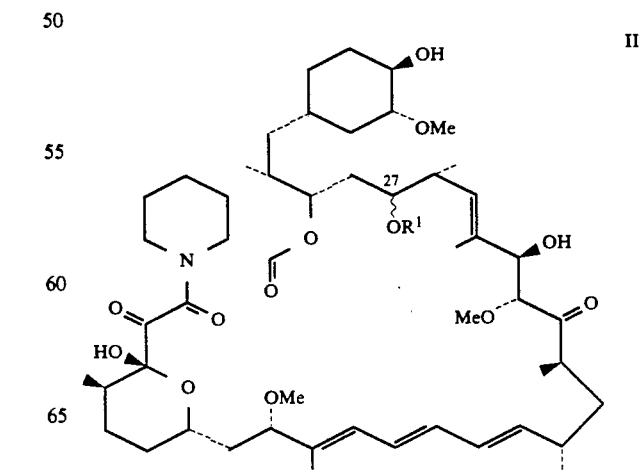

wherein

R¹ is

and

R² is alkyl of 1-10 carbon atoms, arylalkyl of 7-10 carbon atoms, or aryl wherein the aryl group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;

or a pharmaceutically acceptable salt thereof;

or of formula III,

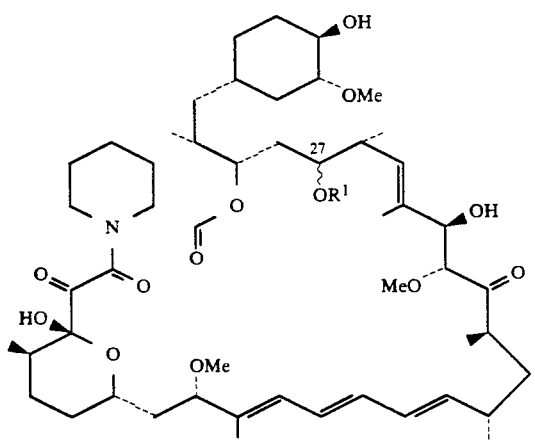

wherein

R¹ is

and

R² is a mono-, di-, poly-, or per-fluorinated alkyl group of 1-10 carbon atoms;

or of formula IV,

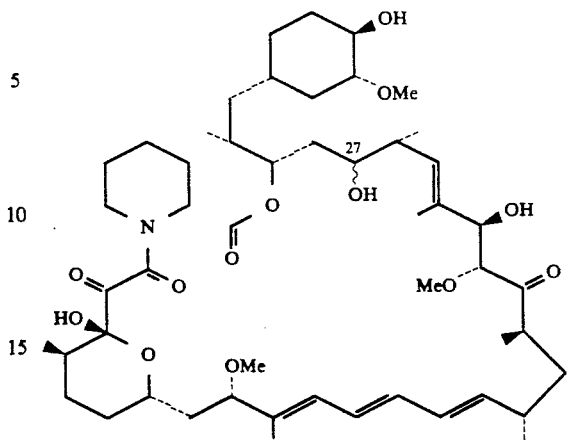

wherein

R¹ is

R² is

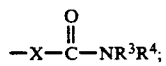

X is —(CH₂)$_m$— or —Ar—;

R³ and R⁴ are each, independently, hydrogen, alkyl of 1-12 carbon atoms, —(CH₂)$_n$—Ar, —(CH₂)$_p$—NR⁵R⁶, or —(CH₂)$_p$—N⁺R⁵R⁶R⁷Y⁻;

R⁵ and R⁶ are each, independently, hydrogen, alkyl of 1-12 carbon atoms, or —(CH₂)$_n$—Ar;

Ar is an optionally mono- or di-substituted group selected from

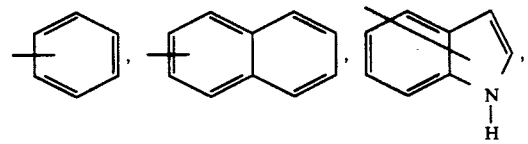

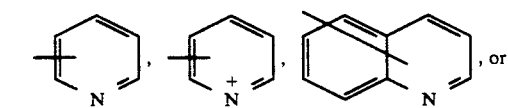

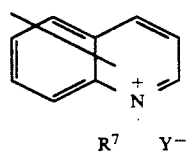

in which the optional substituents are selected from the group consisting of alkyl of 1-6 carbon atoms, arylalkyl of 7-10 carbon atoms, alkoxy of 1-6 carbon atoms, cyano, halo, nitro, carbalkoxy of 2-7 carbon atoms, or perfluoroalkyl of 1-6 carbon atoms;

$R^7$ is alkyl of 1–6 carbon atoms;
Y is a halide, sulfate, phosphate, or p-toluenesulfonate anion;
m=1–6;
n=1–6;
p=1–6;
or a pharmaceutically acceptable salt thereof;
or of formula VI,

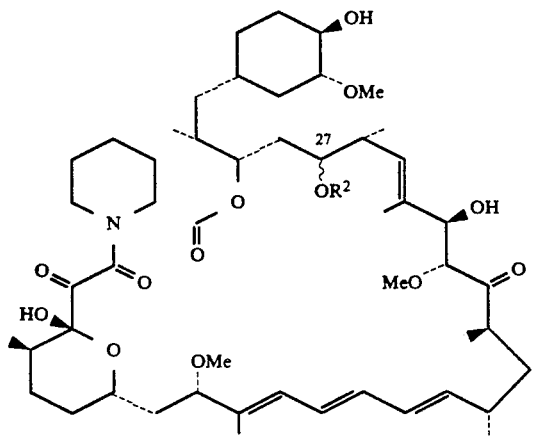

wherein
$R^2$ is

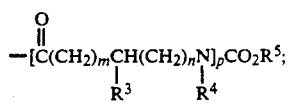

$R^3$ is hydrogen, alkyl of 1–6 carbon atoms, arylalkyl of 7–10 carbon atoms, —$(CH_2)_qCO_2R^6$, —$(CH_2)_rNR^7CO_2R^8$, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indoylmethyl, hydroxyphenylmethyl, imidazoylmethyl or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —$CO_2H$;

$R^4$ and $R^7$ are each, independently, hydrogen, alkyl of 1–6 carbon atoms, or arylalkyl of 7–10 carbon atoms;

$R^5$, $R^6$, and $R^8$ are each, independently, alkyl of 1–6 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —$CO_2H$;

m is 0–4;
n is 0–4;
p is 1–2;
q is 0–4;
r is 0–4;

wherein $R^3$, $R^4$, m, and n are independent in each of the

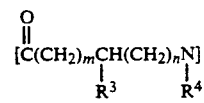

subunits when p=2;
or a pharmaceutically acceptable salt thereof;
or of formula VII,

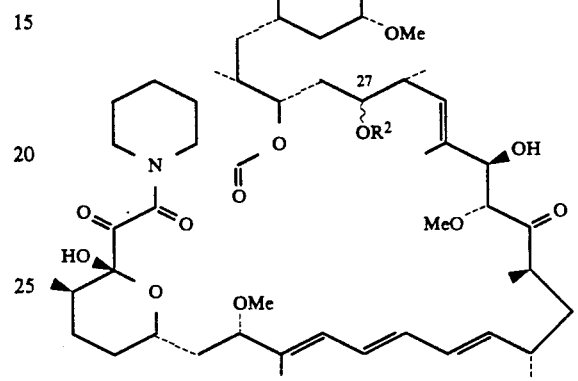

wherein
$R^1$ is alkyl of 1–6 carbon atoms, arylalkyl of 7–10 carbon atoms, —$CH_2YX$, —$C(CH_3)_2YX$, —$CH(CH_3)YX$, or L;
Y is O or S;
X is —$CH_3$, —$(CH_2)_nCH_3$, —$CH_2Ar$, —$(CH_2)_2OCH_3$, —$CH_2CCl_3$, —$CH(CH_3)_2$, or —$CH_2CH_2SiMe_3$;
L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S dioxide; and
n=1–5;
or of formula VIII,

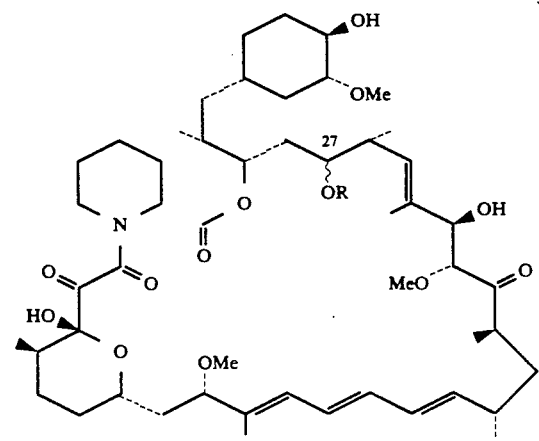

wherein
R is

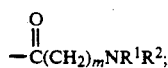

$R^1$ and $R^2$ are each hydrogen or alkyl of 1-3 carbon atoms or $R^1$ and $R^2$ together with the nitrogen to which they are attached form a saturated heterocyclic ring having 4-5 carbon atoms; and m=1-3 or a pharmaceutically acceptable salt thereof; or of formula IX,

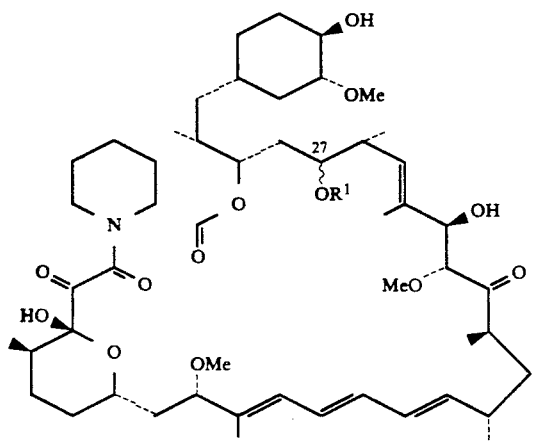

wherein
$R^1$ is —CONHSO$_2$—Ar; and
Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;

or a pharmaceutically acceptable salt thereof when the Ar group contains a basic nitrogen or when the Ar group is substituted by dialkylamino of 1-6 carbon atoms per alkyl group, —SO$_3$H, —PO$_3$H, or —CO$_2$H;

or a pharmaceutically acceptable salt thereof;

or of formula X,

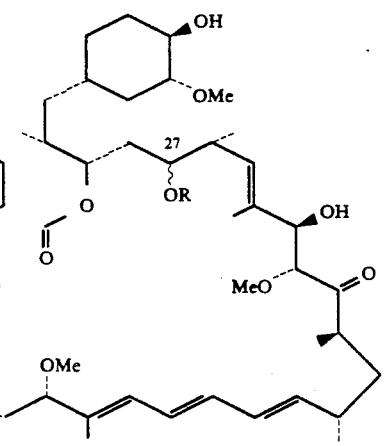

wherein
R is —SO$_2$R$^1$;
$R^1$ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR$^2$; and
$R^2$ is lower alkyl containing 1 to 6 carbon atoms;
or a pharmaceutically acceptable salt thereof,
and a pharmaceutically acceptable carrier.

* * * * *

UNITED STATES PATENT AND TRADEMARK OFFICE
CERTIFICATE OF CORRECTION

PATENT NO. : 5,256,790

DATED : October 26, 1993

INVENTOR(S) : Frances C. Nelson

It is certified that error appears in the above-identified patent and that said Letters Patent is hereby corrected as shown below:

The title page should be deleted and substitute therefor the attached title page.

Columns 11,12, 21,22,23,24,27,28,31,32,33, and 34, should be deleted and substitute therefore the attached pages.

Signed and Sealed this

Fourteenth Day of February, 1995

Attest:

BRUCE LEHMAN

Attesting Officer

Commissioner of Patents and Trademarks

United States Patent [19]

Nelson

[11] Patent Number: 5,256,790
[45] Date of Patent: Oct. 26, 1993

[54] 27-HYDROXYRAPAMYCIN AND DERIVATIVES THEREOF

[75] Inventor: Frances C. Nelson, Yardley, Pa.

[73] Assignee: American Home Products Corporation, New York, N.Y.

[21] Appl. No.: 9,605

[22] Filed: Jan. 27, 1993

Related U.S. Application Data

[63] Continuation-in-part of Ser. No. 930,124, Aug. 13, 1992, abandoned.

[51] Int. Cl.$^5$ .................. C07D 498/16; A61K 31/695
[52] U.S. Cl. ........................................ 514/291; 540/456
[58] Field of Search ........................... 540/456; 514/291

[56] References Cited

U.S. PATENT DOCUMENTS

| | | |
|---|---|---|
| 3,929,992 | 12/1975 | Sehgal et al. |
| 3,993,749 | 11/1976 | Sehgal et al. |
| 4,316,885 | 2/1982 | Rakhit |
| 4,401,653 | 8/1983 | Eng |
| 4,650,803 | 3/1987 | Stella et al. |
| 4,885,171 | 12/1989 | Sehgal et al. |
| 5,078,999 | 1/1992 | Warner et al. |
| 5,080,899 | 1/1992 | Sturm et al. |
| 5,091,389 | 2/1992 | Ondeyka et al. |
| 5,100,883 | 3/1992 | Schiehser |
| 5,100,899 | 3/1992 | Calne |
| 5,102,876 | 4/1992 | Caufield |
| 5,118,677 | 6/1992 | Caufield |
| 5,118,678 | 6/1992 | Kao et al. |
| 5,130,307 | 7/1992 | Failli et al. |
| 5,138,051 | 8/1992 | Hughes et al. |
| 5,147,877 | 11/1992 | Goulet .......................... 540/456 |
| 5,151,413 | 9/1992 | Caufield et al. |
| 5,169,851 | 12/1992 | Hughes et al. |
| 5,177,203 | 1/1993 | Failli et al. |
| 5,194,447 | 3/1993 | Kao |

FOREIGN PATENT DOCUMENTS

507555A1 7/1992 European Pat. Off.

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Meiser, B. J., J. Heart Lung Transplant. 11 (pt. 2):197 (1992).
Stepkowski, S. M., Transplantation Proc. 23:507-8 (1991).

Primary Examiner—Marianne M. Cintins
Assistant Examiner—John Peabody
Attorney, Agent, or Firm—Arnold S. Milowsky

[57] ABSTRACT

This invention provides a compound of formula I,

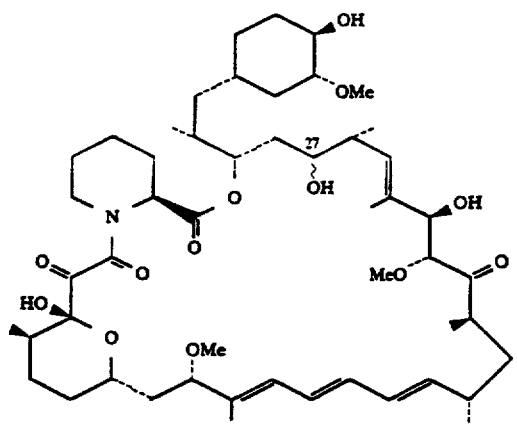

and 27-substituted derivatives thereof which are useful as immunosuppressive, antiinflammatory, antifungal, antitumor, and antiproliferative agents. The compound depicted by formula I is named 27-hydroxyrapamycin, and may also be referred to as 27-deoxo-27-hydroxyrapamycin.

11 Claims, No Drawings

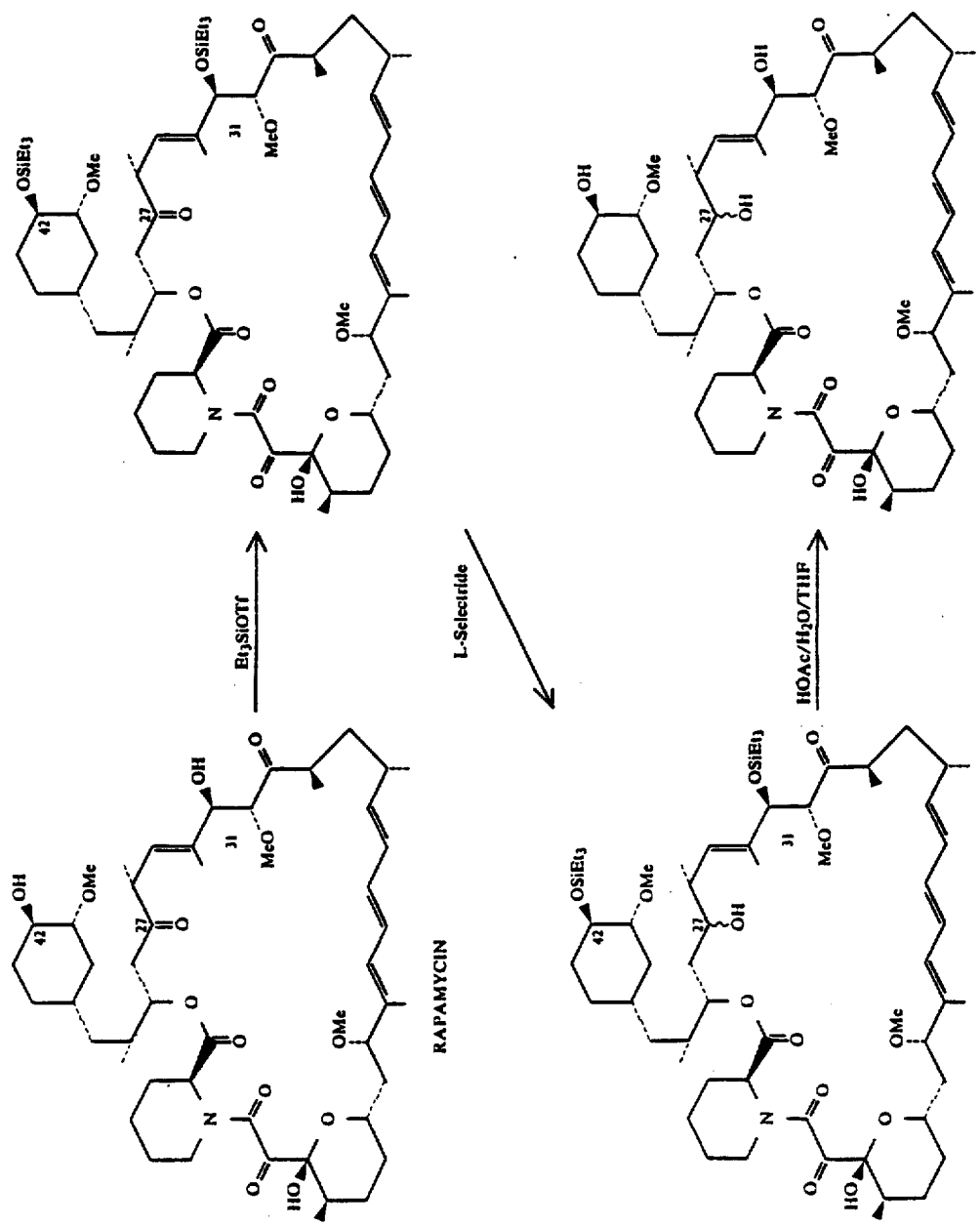

27-Hydroxyrapamycin-27-ester with (2,4-difluorophenyl)carbamic acid

27-Hydroxyrapamycin-27-ester with N-[(1,1-dimethylethoxy)carbonyl]-glycylglycine 27-Hydroxyrapamycin-27-ester with N-[(1,1-dimethylethoxy)carbonyl]-N-methylglycine 27-Hydroxyrapamycin-27-ester with 5-(1,1-dimethylethoxy)-2-[[(1,1-dimethylethoxy)carbonyl]amino]-5-oxopentanoic acid 27-Hydroxyrapamycin-27-ester with 2-[[(1,1-dimethylethoxy)carbonyl]amino]-4-oxo-4-(phenylmethoxy)-butanoic acid 27-Hydroxyrapamycin-27-ester with 3-[[(1,1-dimethylethoxy)carbonyl]amino]-4-oxo-4-(phenylmethoxy)-butanoic acid 27-Hydroxyrapamycin-27-ester with 5-(1,1-dimethyloxy)-4-[[(1,1-dimethylethoxy)carbonyl]amino]-5-oxopentanoic acid 27-Hydroxyrapamycin-27-ester with $N^\alpha$, $N^\epsilon$-bis[(1,1-dimethylethoxy)carbonyl]-L-lysine 27-Hydroxyrapamycin-27-ether with (1-methoxy-1-methyl)ethanol 27-Hydroxyrapamycin-27-ether with (2-(trimethylsilyl)ethoxy)methanol 27-Hydroxyrapamycin-27-ester with N,N-dimethylglycine 27-Hydroxyrapamycin-27-ester with 3-(N,N-diethylamino)propionic acid 27-Hydroxyrapamycin-27-ester with 4'-(N-pyrrolidino)butyric acid 27-Hydroxyrapamycin-27-ester with phenylsulfonylcarbamic acid 27-Hydroxyrapamycin-27-ester with (4-chlorophenylsulfonyl)carbamic acid 27-Hydroxyrapamycin-27-ester with (3-methylphenylsulfonyl)carbamic acid 27-Hydroxyrapamycin-27-ester with 5-(dimethylamino)-1-naphthalensulfonic acid 27-Hydroxyrapamycin-27-ester with 4-methylbenzenesulfonic acid 27-Hydroxyrapamycin-27-ester with 2-thiophenesulfonic acid 27-Hydroxyrapamycin-27-ester with 4-[[4-(dimethylamino)phenyl]aza]benzenesulfonic acid 27-Hydroxyrapamycin-27-ester with 1-naphthalenesulfonic acid 27-Hydroxyrapamycin-27-ester with 8-quinolinsulfonic acid 27-Hydroxyrapamycin-27-ester with methanesulfonic acid 27-Hydroxyrapamycin-27-ester with 2,2,2-trifluoroethanesulfonic acid 27-Hydroxyrapamycin-27-ester with [(methoxycarbonyl)amino]sulfonic acid

What is claimed is:

1. A compound of the formula

wherein
$R^1$ is $$-\overset{O}{\underset{\|}{C}}R^2$$

and
$R^2$ is alkyl of 1–10 carbon atoms, arylalkyl of 7–10 carbon atoms, or aryl wherein the aryl group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO₃H, —PO₃H, and —CO₂H;
or a pharmaceutically acceptable salt thereof.

2. A compound of claim 1 which is 27-hydroxyrapamycin-27-ester with acetic acid.

3. A compound of the formula

wherein
$R^1$ is $$-\overset{O}{\underset{\|}{C}}R^2$$

and $R^2$ is a mono-, di-, poly-, or per-fluorinated alkyl group of 1-10 carbon atoms.

4. A compound of the formula

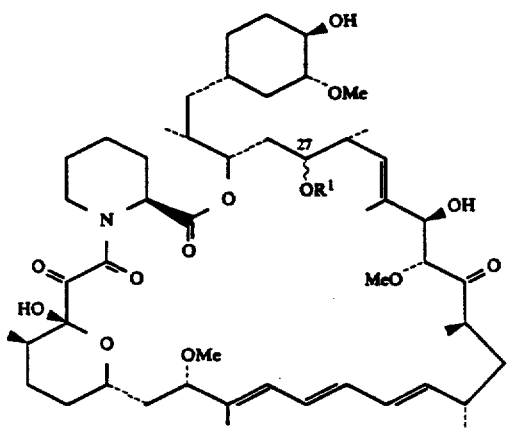

IV wherein
$R^1$ is

$R^2$ is

X is —$(CH_2)_m$— or —Ar—;

$R^3$ and $R^4$ are each, independently, hydrogen, alkyl of 1-12 carbon atoms, —$(CH_2)_n$—Ar, —$(CH_2)_p$—$NR^5R^6$, or —$(CH_2)_p$—$N^+R^5R^6R^7Y^-$;

$R^5$ and $R^6$ are each, independently, hydrogen, alkyl of 1-12 carbon atoms, or —$(CH_2)_n$—Ar;

Ar is an optionally mono- or di-substituted group selected from

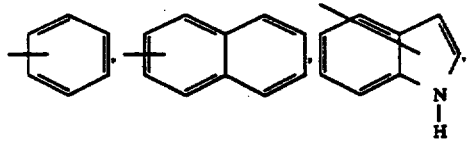

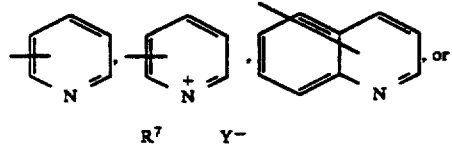

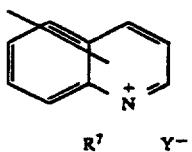

in which the optional substituents are selected from the group consisting of alkyl of 1-6 carbon atoms, arylalkyl of 7-10 carbon atoms, alkoxy of 1-6 carbon atoms, cyano, halo, nitro, carbalkoxy of 2-7 carbon atoms, or perfluoroalkyl of 1-6 carbon atoms;

$R^7$ is alkyl of 1-6 carbon atoms;

Y is a halide, sulfate, phosphate, or p-toluenesulfonate anion;

m=1-6;
n=1-6;
p=1-6;

or a pharmaceutically acceptable salt thereof.

5. A compound of the formula

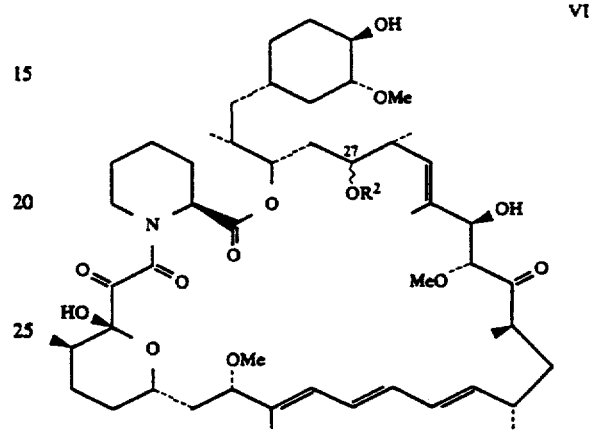

VI wherein
$R^2$ is

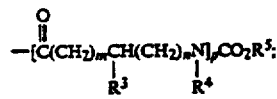

$R^3$ is hydrogen, alkyl of 1-6 carbon atoms, arylalkyl of 7-10 carbon atoms, —$(CH_2)_qCO_2R^6$, —$(CH_2)_rNR^7CO_2R^8$, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —$CO_2H$;

$R^4$ and $R^7$ are each, independently, hydrogen, alkyl of 1-6 carbon atoms, or arylalkyl of 7-10 carbon atoms;

$R^5$, $R^6$, and $R^8$ are each, independently, alkyl of 1-6 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —$CO_2H$;

m is 0-4;
n is 0-4;
p is 1-2;
q is 0-4;
r is 0-4;

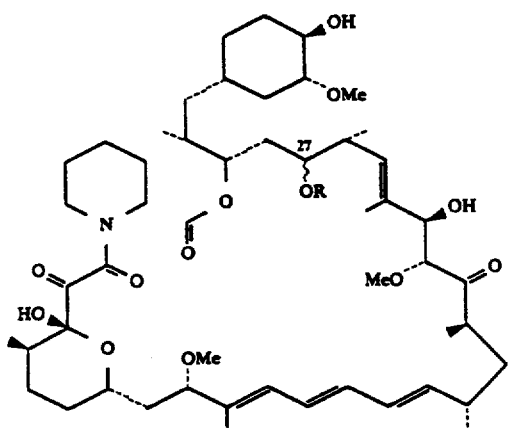

wherein
R is —SO₂R¹;
R¹ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR²; and
R² is lower alkyl containing 1 to 6 carbon atoms; or a pharmaceutically acceptable salt thereof.

10. A method of inducing immunosuppression which comprises administering an immunosuppressive effective amount of a compound of formula II,

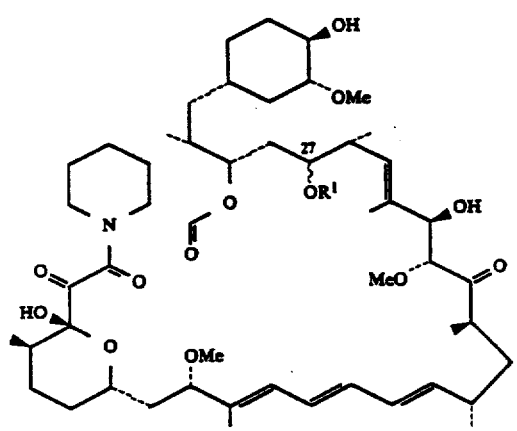

wherein
R¹ is

and
R² is alkyl of 1-10 carbon atoms, arylalkyl of 7-10 carbon atoms, or aryl wherein the aryl group may be optionally mono-, di-, or tri- substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;
or a pharmaceutically acceptable salt thereof;
or of formula III,

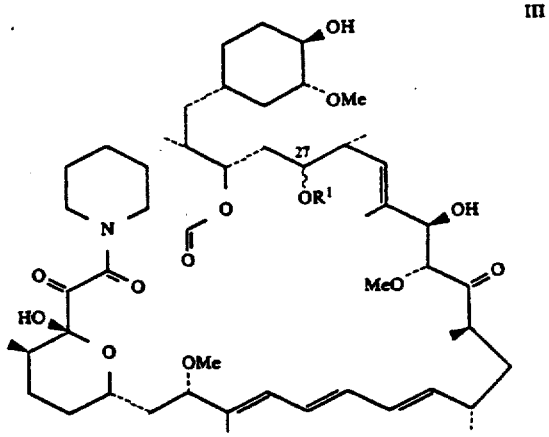

wherein
R¹ is

and
R² is a mono-, di-, poly-, or per-fluorinated alkyl group of 1-10 carbon atoms;
or of formula IV,

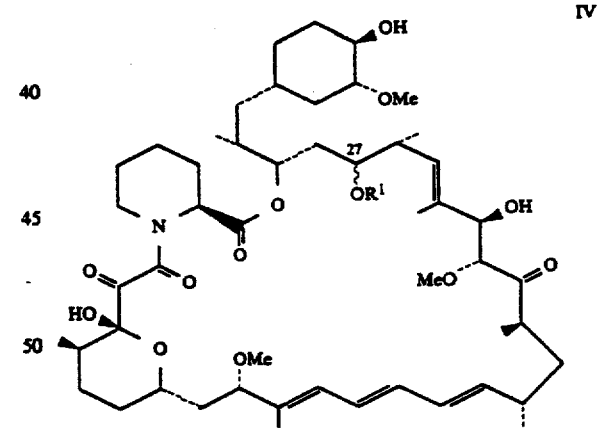

wherein
R¹ is

R² is

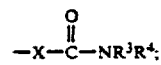

X is —(CH₂)ₙ— or —Ar—;

$R^1$ is alkyl of 1–6 carbon atoms, arylalkyl of 7–10 carbon atoms, —CH$_2$YX, —C(CH$_3$)$_2$YX, —CH(CH$_3$)YX, or L;

Y is O or S;

X is —CH$_3$, —(CH$_2$)$_n$CH$_3$, —CH$_2$Ar, —(CH$_2$)$_2$OCH$_3$, —CH$_2$CCl$_3$, —CH(CH$_3$)$_2$, or —CH$_2$CH$_2$SiMe$_3$;

L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S dioxide; and n = 1–5;

or of formula VIII,

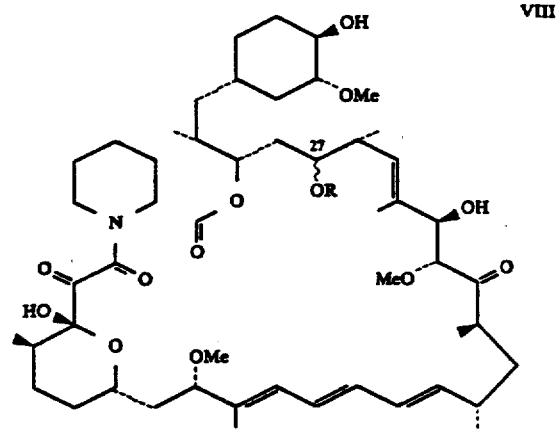

wherein R is

$R^1$ and $R^2$ are each hydrogen or alkyl of 1–3 carbon atoms or $R^1$ and $R^2$ together with the nitrogen to which they are attached form a saturated heterocyclic ring having 4–5 carbon atoms; and m = 1–3 or a pharmaceutically acceptable salt thereof; or of formula IX,

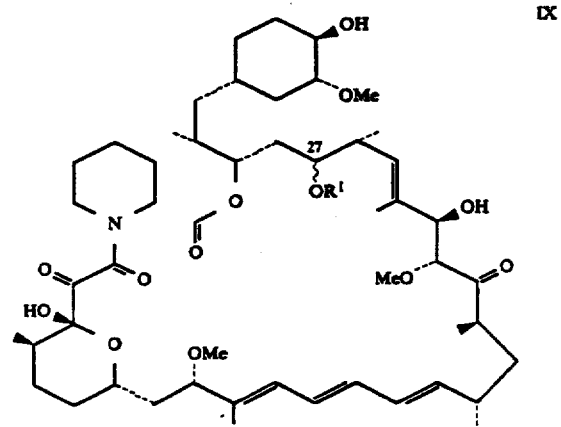

wherein
$R^1$ is —CONHSO$_2$—Ar; and

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H;

or a pharmaceutically acceptable salt thereof when the Ar group contains a basic nitrogen or when the Ar group is substituted by dialkylamino of 1–6 carbon atoms per alkyl group, —SO$_3$H, —PO$_3$H, or —CO$_2$H;

or a pharmaceutically acceptable salt thereof;

or of formula X,

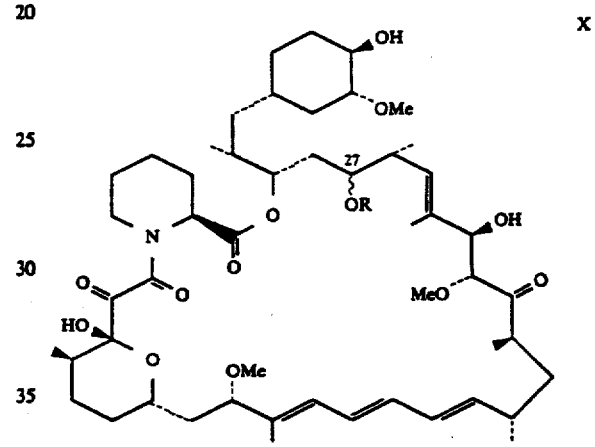

wherein
R is —SO$_2$R$^1$;

$R^1$ is alkyl, alkenyl, alkynyl containing 1 to 6 carbon atoms; or an aromatic moiety selected from the group consisting of phenyl and naphthyl or a heterocyclic moiety selected from the group consisting of thiophenyl and quinolinyl; or —NHCOR$^2$; and $R^2$ is lower alkyl containing 1 to 6 carbon atoms; or a pharmaceutically acceptable salt thereof.

11. A pharmaceutical composition which comprises an effective amount of a compound of formula II,

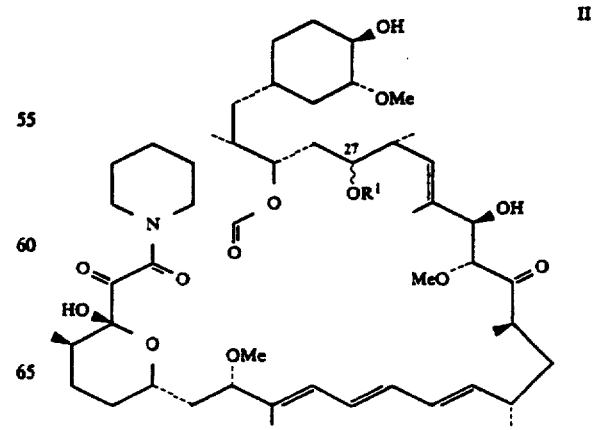

wherein

R¹ is

and

R² is alkyl of 1–10 carbon atoms, arylalkyl of 7–10 carbon atoms, or aryl wherein the aryl group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO₃H, —PO₃H, and —CO₂H;

or a pharmaceutically acceptable salt thereof;
or of formula III,

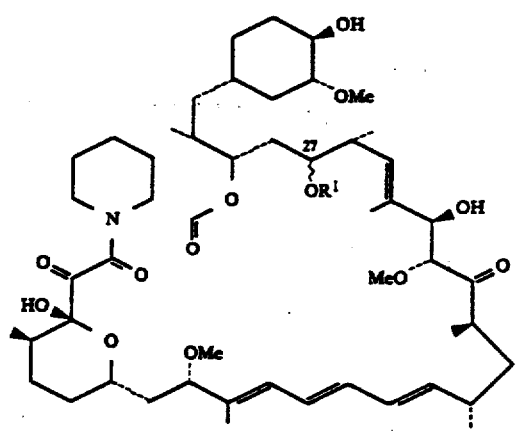

wherein

R¹ is

and

R² is a mono-, di-, poly-, or per-fluorinated alkyl group of 1–10 carbon atoms;

or of formula IV,

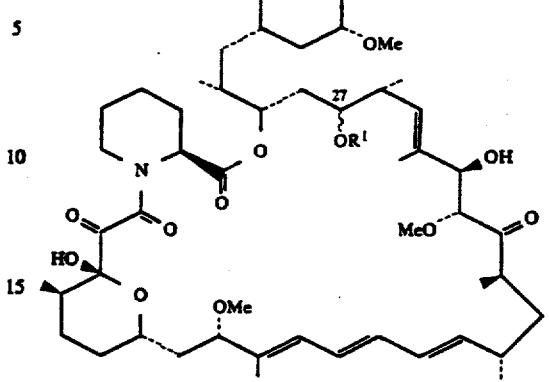

wherein

R¹ is

R² is

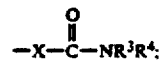

X is —(CH₂)ₘ— or —Ar—;

R³ and R⁴ are each, independently, hydrogen, alkyl of 1–12 carbon atoms, —(CH₂)ₙ—Ar, —(CH₂)ₚ—NR⁵R⁶, or —(CH₂)ₚ—N⁺R⁵R⁶R⁷Y⁻;

R⁵ and R⁶ are each, independently, hydrogen, alkyl of 1–12 carbon atoms, or —(CH₂)ₙ—Ar;

Ar is an optionally mono- or di-substituted group selected from

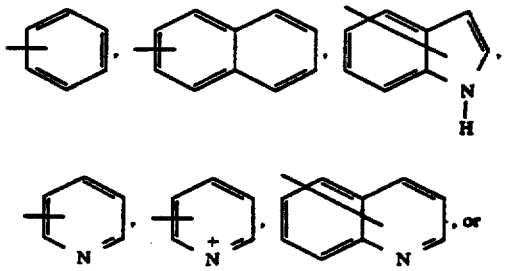

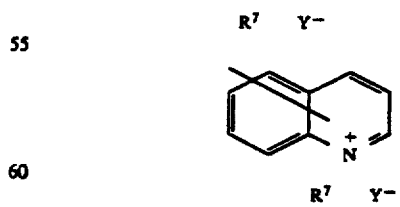

in which the optional substituents are selected from the group consisting of alkyl of 1–6 carbon atoms, arylalkyl of 7–10 carbon atoms, alkoxy of 1–6 carbon atoms, cyano, halo, nitro, carbalkoxy of 2–7 carbon atoms, or perfluoroalkyl of 1–6 carbon atoms;